United States Patent
Frei et al.

(10) Patent No.: US 9,766,235 B2
(45) Date of Patent: Sep. 19, 2017

(54) TRIFUNCTIONAL CROSSLINKING REAGENTS

(75) Inventors: Andreas Frei, Zurich (CH); Bernd Wollscheid, Zurich (CH); Ock-Youm Jeon, Zurich (CH); Erick Carreira, Zumikon (CH)

(73) Assignee: ETH Zurich, Zurich (CH)

(*) Notice: Subject to any disclaimer, the term of this patent is extended or adjusted under 35 U.S.C. 154(b) by 708 days.

(21) Appl. No.: 13/982,596

(22) PCT Filed: Jan. 30, 2012

(86) PCT No.: PCT/EP2012/000392
§ 371 (c)(1),
(2), (4) Date: Sep. 25, 2013

(87) PCT Pub. No.: WO2012/104051
PCT Pub. Date: Aug. 9, 2012

(65) Prior Publication Data
US 2014/0011212 A1  Jan. 9, 2014

(30) Foreign Application Priority Data
Jan. 31, 2011  (EP) .................................... 11000731

(51) Int. Cl.
G01N 33/566 (2006.01)
C07D 495/04 (2006.01)
G01N 33/58 (2006.01)

(52) U.S. Cl.
CPC ......... *G01N 33/566* (2013.01); *C07D 495/04* (2013.01); *G01N 33/582* (2013.01); *G01N 2333/70596* (2013.01); *Y02P 20/55* (2015.11)

(58) Field of Classification Search
CPC .................................................. G01N 33/566
See application file for complete search history.

(56) References Cited

PUBLICATIONS

Cuatrecasas et al., Adsorbents for Affinity Chromatography. Use of N-Hydroxysuccinimide Esters of Agarose, vol. 11, No. 12, pp. 2291-2298, 1972.*
International Search Report for corresponding International Application No. PCT/EP2012/000392 dated Apr. 18, 2012.
Pfander et al., "Reversible site-specific tagging of enzymatically synthesized RNAs using aldehyde-hydrazine chemistry and protease-cleavable linkers", Nucleic Acids Research, vol. 35, No. 4, Jan. 26, 2007, pp. 1-8.
Pfander et al., "Supplementary Data: Reversible site-specific tagging of enzymatically synthesized RNAs using aldehyde-hydrazine chemistry and protease-cleavable linkers", Nucleic Acids Research, 2007, pp. S1-S8.
Varki et al., Chapter 26, "Discovery and Classification of Glycan-Binding Proteins", 2009, pp. 375-376 (cited in specification on p. 1).

(Continued)

*Primary Examiner* — Mark Shibuya
*Assistant Examiner* — Nam Nguyen
(74) *Attorney, Agent, or Firm* — Renner, Otto, Boisselle & Sklar, LLP

(57) ABSTRACT

The present invention relates to trifunctional crosslinking reagents carrying (i) a ligand-reactive group for conjugation to a ligand of interest having at least one binding site on a target glycoprotein receptor, (ii) an optionally protected aromatic hydrazine group for the capturing of oxidized receptor-glycopeptides and (iii) an affinity group for the detection, isolation and purification of captured glycopeptides, their methods of production, as well as their use in methods for detecting, identifying and characterizing interactions between ligands and their corresponding glycoprotein target receptors on living cells and in biological fluids.

14 Claims, 3 Drawing Sheets

(56) References Cited

PUBLICATIONS

Sinz, "Chemical cross-linking and mass spectrometry for mapping three-dimensional structures of proteins and protein complexes", Journal of Mass Spectrometry, vol. 38, 2003, pp. 1225-1237 (cited in specification on p. 2).

Sinz et al., "Mapping Protein Inferfaces by a Trifunctional Cross-Linker combined with MADLI-TOP and ESI-FTICR Mass spectrometry", Journal American Society Mass , vol. 16, 2005, pp. 1921-1931 (cited in specification on p. 3).

Mueller et al., "SuperHirn—a novel tool for high resolution LC-MS-based peptide/protein profiling", Proteomics, vol. 7, 2007, pp. 3470-3480 (cited in specification on p. 41).

Nilsson et al., "Mass spectrometry in high-throughput proteomics: ready for the big time", Nature Methods, vol. 7, No. 9, Sep. 2010, pp. 681-685 (cited in specification on p. 41).

Glenn et al., "conformationally Homogeneous Cyclic Tetrapeptides: Useful New Three-Dimensional Scaffolds", Journal American Chemical Society, vol. 125, 2003, pp. 640-641 (cited in specification on p. 43).

Srinvasan et al., "Functionalization of Magnetic Nanoparticles with Organic Molecules: Loading Level Determination and Evaluation of Linker Length Effect on Immobilization", Chirality, vol. 20, 2008, pp. 265-277 (cited in specification on p. 43).

Abrams et al., "Technetium-99m-Human Polyclonal IgG Radiolabeled via the Hydrazino Nicotinamide Derivative for Imaging Focal Sites of Infection in Rats", The Journal of Nuclear Medicine, vol. 31, No. 12, Dec. 1990, pp. 2022-2028 (cited in specification on p. 47).

* cited by examiner

US 9,766,235 B2

TRIFUNCTIONAL CROSSLINKING REAGENTS

This application is a national phase of International Application No. PCT/EP2012/000392 filed Jan. 30, 2012, and published in the English language which claims priority to EP 11000731.7 filed Jan. 31, 2011.

FIELD OF THE INVENTION

The present invention relates to trifunctional crosslinking reagents carrying (i) a ligand-reactive group for conjugation to a ligand of interest having at least one binding site on a target glycoprotein receptor, (ii) an optionally protected aromatic hydrazine group for the capturing of oxidized receptor-glycopeptides (iii) an affinity group for the detection, isolation and purification of captured glycopeptides, their methods of production, as well as their use in methods for detecting, identifying and characterizing interactions between ligands and their corresponding glycoprotein target receptors on living cells and in biological fluids.

BACKGROUND OF THE INVENTION

Glycosylation is one of the most prominent protein modifications and many if not most secretory and membrane-bound proteins produced by mammalian cells contain covalently linked glycans (Varki, A. et al. Essentials of Glycobiology, Cold Spring Harbor Laboratory Press, 2009). In the assembly of complex organisms such oligosaccharide portions serve a variety of structural and functional roles for the folding, subcellular localization, turnover, activity and interactions of secreted and cell surface proteins.

Secreted glycoproteins include e.g. cytokines, hormones, growth and differentiation factors, enzymes, neuropeptides, vasomediators, antigen recognition molecules, immunoregulatory molecules, structural glycoproteins, and other bioactive molecules. Those proteins are important in many recognition events, such as cell-to-cell signaling, immune responses, apoptosis, host-pathogen interactions and the pathogenesis of many diseases. Thereby, the specificity of such glycoproteins for certain target receptors is essential in regulating cell-to-cell communication. Thus the identification and characterization of ligand binding interactions of secreted glycoproteins with their targets is essential for a molecular understanding of biological information transfer.

In analogy, the engagement of cell surface glycoprotein receptors (CSRs) by ligands, such as proteins, peptides, hormones, chemical molecules, pharmaceutical drugs or toxins enables the transfer of information from the cellular microenvironment into the cell. Despite the fact that this cell surface information gateway is critical for cellular responses, the receptors for many functional ligands remain unknown. This is mainly due to technological limitations in the identification of hydrophobic membrane receptor proteins and due to transient, low affinity interactions of ligands with their corresponding CSRs. Therefore, many signaling proteins and molecules remain orphan ligands without a known primary molecular target—invaluable information currently missing for a detailed molecular understanding of the respective mechanisms of signal transduction, drug action, off-target effects or disease-associated signaling networks.

A promising approach to the identification of transient ligand-receptor interactions in biological systems is the chemical crosslinking of interacting molecules followed by mass spectrometric identification of the interaction partners. Currently known and commercially available crosslinkers have typically been designed for their use in mapping protein interfaces with isolated proteins in solution. For example, homobifunctional or heterobifunctional crosslinkers (including cleavable or isotope-encoded derivatives) have been used for the chemical crosslinking of proteins followed by enzymatic digestion and mass spectrometric identification of the crosslinked peptides for mapping three-dimensional structures of proteins and protein complexes (JMS (2003) vol. 38 (12) pp. 1225-37). However, the crosslinked peptide species obtained with such molecules are typically of very low relative abundance and the bioinformatic analysis of the mass spectra produced by crosslinked peptides remains a daunting task. This hampers the identification of crosslinking sites in complex biological samples, in particular for the detection of typically transient interactions of ligands with their corresponding receptors.

In order to specifically enrich crosslinked peptides out of complex samples, trifunctional crosslinkers have been disclosed having a combination of two reactive sites (typically amine-reactive, sulfhydryl-reactive or photoreactive) to capture interacting proteins, and an affinity group (typically biotin) for the subsequent enrichment of captured peptides (J Am Soc Mass Spectrom (2005) vol. 16 (12) pp. 1921-31). While these crosslinkers have been used successfully for the mapping of topological structures of isolated proteins and protein complexes, their chemical nature renders them unsuitable for the detection of transient protein-protein interactions in complex samples derived from live cells.

This highlights the need for suitable reagents that are able to aid specifically in the probing, identification, and characterization of ligand interactions with target glycoprotein receptors in their biological microenvironment, such as in biological fluids or associated with the plasma membrane of living cells. To applicant's best knowledge, neither of the known crosslinkers today is able to fulfill the structural requirements for enabling the covalent stabilization and subsequent mass-spectrometric identification of specific interactions between a known ligand and unknown glycoprotein receptor binding partners in a complex and natural environment, such as the surface of a living cell.

Applicants have now found that a novel class of trifunctional crosslinking reagents, hereinafter also called crosslinkers of the invention, are able to overcome the problems inherent to the ligand-based identification of target receptors of the prior art. The crosslinkers of the invention can be used for the unbiased detection and characterization of ligand-receptor interactions between a ligand and a target glycoprotein receptor with high sensitivity and specificity on live cells or in biological fluids applying near-physiological conditions. This method can thus be applied to identify unknown target receptors for orphan ligands such as proteins, peptides, lipids, engineered affinity binders, chemical molecules, drugs, viruses or bacteria. Thus, the new crosslinking reagents provide a technological basis for the understanding of the human surfaceome and secretome as a complex information gateway and a means to identify target glycoprotein receptors for orphan ligands of almost every description within their native microenvironment.

SUMMARY OF THE INVENTION

The present invention is directed in a first aspect towards a trifunctional crosslinking reagent having a core structure carrying three branches, wherein each branch comprises a different functionality (and thus the crosslinking reagent may also be termed heterotrifunctional). A first branch comprises a protected or unprotected aromatic hydrazine that is able to react with oxidized glycoproteins. A second branch comprises a ligand-reactive group that may be conjugated to a ligand of choice. A third branch comprises an affinity group for purification purposes, preferably affinity purification purposes of the peptides captured by the first and second functionality. These reagents are of special interest as the combination of these three different functionalities in one molecule is unique and finds use in various biomedical applications such as the detection and characterization of interactions between a ligand and a target glycoprotein receptor.

More specifically, the invention is directed towards a trifunctional crosslinking reagent of formula I:

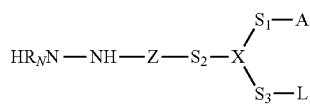

wherein
X is a core structure;
A is an affinity group
$S_1$, $S_2$, $S_3$ are independently of each other a spacer group;
L is a ligand-reactive group;
Z is aryl or heteroaryl, and
$R_N$ is H or a hydrazine-protecting group.

In preferred embodiments X is a group of formula II

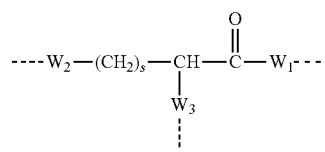

wherein the dotted lines represent the linkage of $W_1$, $W_2$, $W_3$ to groups $S_1$, $S_2$, $S_3$, $W_1$ is —NH—, —O—, —S—, and
$W_2$, $W_3$ are independently of each other a functional group selected from —COO—, —OOC—, —CONH—, —NHCO, —NH—, —O—, —S—, and s is from 1 to 12.

In some embodiments, L is (i) a reactive functional group, preferably selected from the group consisting of —COOH, —NH$_2$, —OH, —SH, —CH═CH— and —CH═CH—COOH, or (ii) an activated functional group selected from the group consisting of an amine-reactive group, a hydroxyl-reactive group, a thiol-reactive group, an aldehydro- or keto-reactive group, and a carboxy-reactive group.

In other embodiments, A is an affinity group, such as biotin.

In further embodiments, the spacer groups $S_1$, $S_2$, $S_3$ are independently of each other (i) a single bond or (ii) a straight-chain or branched, substituted or unsubstituted C(1-24)alkylene, wherein one or more, preferably non-adjacent, —CH$_2$— groups may independently from each other be replaced by one or more bridging groups and/or an unsubstituted or substituted cycloalkyl, heterocycloalkyl, aryl, heteroaryl; with the proviso that heteroatoms, such as O and N, are not directly linked to each other.

In specific embodiments, the trifunctional crosslinking reagent of the invention has a structure of formula III

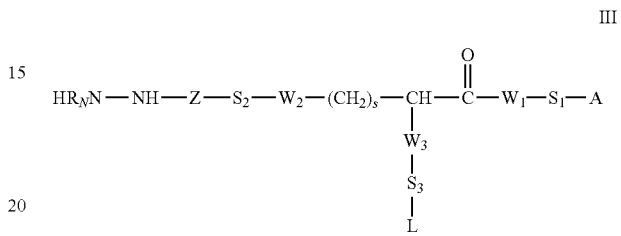

wherein
A is an affinity group;
L is a ligand-reactive group,
$S_1$, $S_2$, $S_3$ are independently of each other a spacer group;
Z is aryl or heteroaryl,
$R_N$ is H or a hydrazine-protecting group
$W_1$ is —NH—, —O—, —S—,
$W_2$, $W_3$ are independently of each other a functional group selected from —COO—, —OOC—, —CONH—, —NHCO, —NH—, —O—, —S—, and
s is from 1 to 12.

In preferred embodiments, the trifunctional crosslinking reagent of the invention has a structure of formula VII

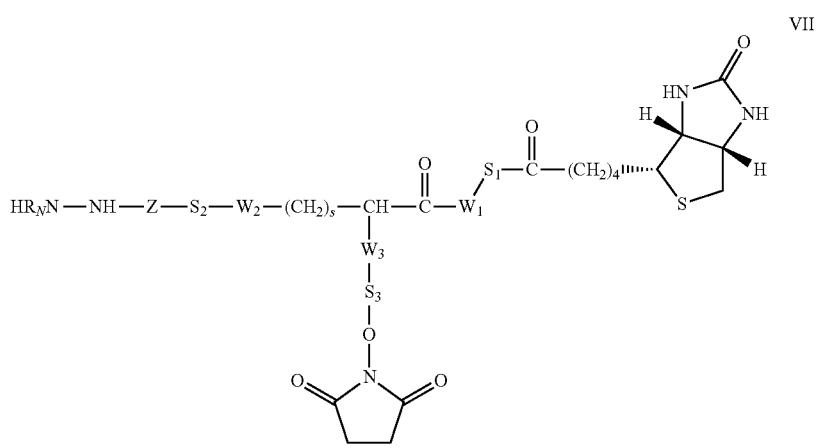

wherein
$S_1$, $S_2$, $S_3$ are independently of each other a spacer group;
$W_1$ is —NH—, —O—, —S—,
$W_2$, $W_3$ are independently of each other a functional group selected from —COO—, —OOC—, —CONH—, —NHCO, —NH—, —O—, —S—
Z is aryl or heteroaryl,
$R_N$ is H or a hydrazine-protecting group, and
s is from 1 to 12.

In another aspect the invention is also directed towards the use of a trifunctional crosslinking reagent of the invention for characterizing and analyzing interactions between a ligand and a target glycoprotein receptor, such as a cell surface or secreted glycoprotein receptor.

In yet another aspect the invention is also directed towards a method of identifying specific interactions between a ligand and a target glycoprotein receptor having at least one carbohydrate residue in a sample, wherein the ligand recognizes a ligand-specific domain on the target glycoprotein receptor, comprising the steps of:

i) providing a sample comprising said target glycoprotein receptor, ii) subjecting the target glycoprotein receptor to oxidative treatment to generate aldehyde functions on the at least one carbohydrate residue thereby obtaining an oxidized target glycoprotein receptor, iii) providing a trifunctional crosslinking reagent according to the invention carrying on three different branches a (protected) hydrazine group, a ligand-reactive group, an affinity group (such as a trifunctional crosslinking reagent according to formulas I, III, V, VI, VII, VIII, IX, and allowing the ligand-reactive group to conjugate to said ligand to obtain a ligand-crosslinking reagent-complex, iv) contacting the sample with the ligand-crosslinking reagent-complex under conditions under which (a) the ligand is able to bind to the ligand-specific domain on the target glycoprotein receptor and (b) the protected hydrazine group is converted to its free form and allowed to react with the oxidized target glycoprotein receptor, to obtain a dual peptide-bound complex, v) isolating and purifying the dual peptide-bound complex from the sample, vi) releasing the peptides from the purified dual peptide-bound complex obtained in step (iv) to obtain released peptides and vii) analyzing and quantifying the released peptides obtained in step (v) by high mass accuracy mass spectrometry, and viii) identifying the interactions between the ligand and the target glycoprotein receptor through quantitative comparison to a control reaction.

In yet a further aspect the invention is also directed towards a kit comprising a trifunctional crosslinking reagent according to the invention carrying on three different branches a (protected) hydrazine group, a ligand-reactive group, and an affinity group, such as a trifunctional crosslinking reagent as defined herein.

DETAILED DESCRIPTION

Figure 1:
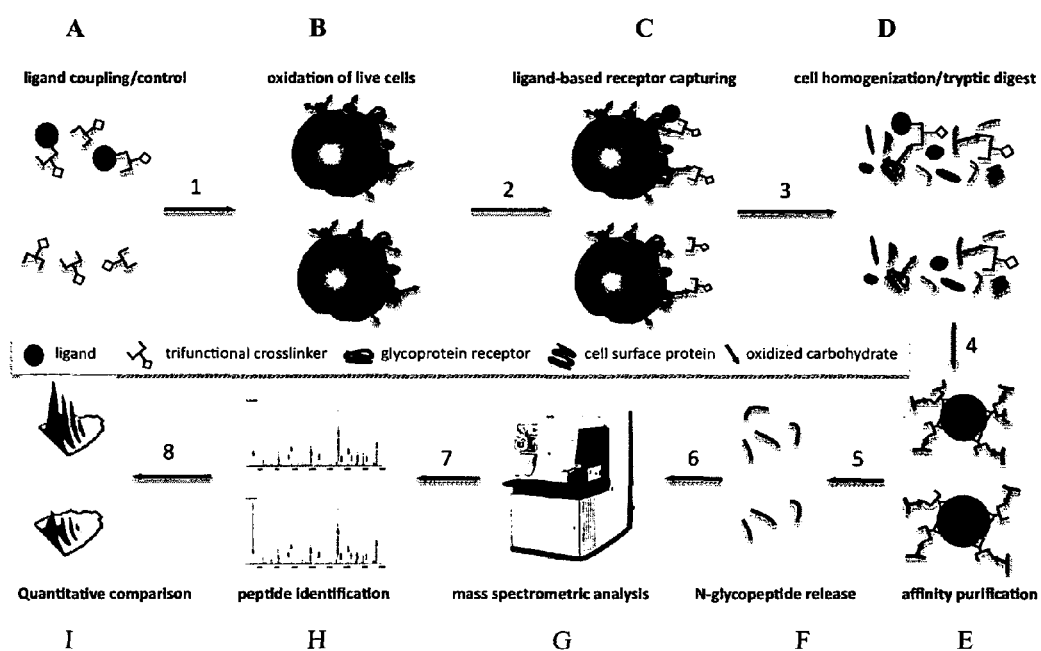
FIG. 1: Schematic illustration of the ligand-based receptor capturing workflow of cell surface target glycoprotein receptors

Unless defined otherwise, the following definitions are used throughout the description:

The term "a" as used herein, refers to at least one, unless otherwise mentioned. The term "include" as used herein, refers to includes without limitation. The term "plurality" refers to a number of two or more.

The term "trifunctional" means "carrying three functionalities". Thus a trifunctional (crosslinking) reagent refers to a (crosslinking) reagent having three functionalities. The term "heterotrifunctional" means "carrying three different functionalities".

The term "(interactive) binding" or "interaction" refers to any type of interactive association between a corresponding pair of molecules (e.g., ligand/target glycoprotein receptor) that exhibit mutual affinity or binding capacity. An interactive association may occur e.g. between a corresponding pair of chemically reactive groups (donor/acceptor, acid/base, etc) that exhibit mutual reactivity. Exemplary binding events include, without limitation, hydrophobic interactions, hydrophilic interactions, hydrogen bonds, van der Waals forces, ionic interactions, nonionic interactions, electrostatic interactions, covalent bonding, and the like. It is understood that depending of the nature of the binding event the interaction may be of different levels, i.e. transient or permanent, weak or strong binding.

The present invention is directed towards novel heterotrifunctional crosslinkers and their application in straightforward quantitative mass spectrometric workflows for the unbiased detection of ligand interactions with target glycoprotein receptors, which include plasma membrane glycoproteins on live cells or secreted glycoproteins.

Thus in a first aspect, the present invention is directed towards a trifunctional crosslinking reagent having a core structure carrying three branches, wherein each branch comprises a different functionality (and thus the crosslinking reagent may also be termed heterotrifunctional). A first branch comprises a protected or unprotected aromatic hydrazine that is able to react with oxidized glycoproteins. A second branch comprises a ligand-reactive group that may be conjugated to a ligand of choice. A third branch comprises an affinity group for purification purposes, preferably affinity purification purposes of the peptides captured by the first and second functionality. These reagents are of special interest as the combination of these three different functionalities in one molecule is unique and finds use in various biomedical applications such as the detection and characterization of interactions between a ligand and a target glycoprotein receptor.

More specifically, the present invention provides a trifunctional crosslinking reagent of formula I:

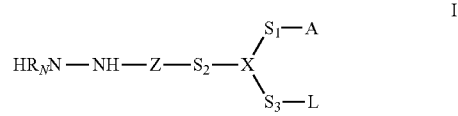

wherein X is a core structure; $S_1$, $S_2$, $S_3$ are independently of each other a spacer group; L is a ligand-reactive group; A is an affinity group; Z is aryl or heteroaryl and $R_1$ is H or a hydrazine-protecting group.

The term "alkyl" as used herein refers to a straight or branched hydrocarbon containing 1-24, preferably 1 to 12 carbon atoms. Examples of alkyl groups include, but are not limited to, methyl, ethyl, n-propyl, i-propyl, n-butyl, i-butyl, and t-butyl, pentyl, hexyl. The term "alkoxy" refers to an —O-alkyl group.

The term "alkylene" as used herein refers to a divalent radical derived from a hydrocarbon, for example —CHR—(CHR)$_n$— with R being H or a substituent of choice. Typically, an alkylene group will have from 1 to 24 carbon atoms (i.e. n=24), preferably 10 to 24 carbon atoms. The term "heteroalkylene" as used herein refers to an alkylene having one or more heteroatoms, such as O, N or S, preferably O or N, inserted into the alkylradicals.

The term "aryl" as used herein refers to a 6-carbon monocyclic, 10-carbon bicyclic, 14-carbon tricyclic aromatic ring system wherein each ring may have unsubstituted or 1 to 4 substituents. Examples of aryl groups include, but are not limited to, phenyl, naphthyl, and anthracenyl. Phenylene, as used in the context of the present invention, preferably denotes a 1,2-, 1,3- or 1,4-phenylene group, which is optionally substituted.

The term "cycloalkyl" refers to a saturated and partially unsaturated cyclic hydrocarbon group having 3 to 12 carbons. Examples of cycloalkyl groups include, but are not limited to, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having one or more heteroatoms (such as O, N, or S). Examples of heteroaryl groups include pyridyl, furyl, imidazolyl, benzimidazolyl, pyrimidinyl, thienyl, quinolinyl, indolyl, and thiazolyl. Pyridyl includes 2-pyridyl, 3-pyridyl and 4-pyridyl, preferably 2-pyridyl. The term "heteroaralkyl" refers to an alkyl group substituted with a heteroaryl group.

The term "heterocycloalkyl" refers to a nonaromatic 5-8 membered monocyclic, 8-12 membered bicyclic, or 11-14 membered tricyclic ring system having one or more heteroatoms (such as O, N, or S). Examples of heterocycloalkyl groups include, but are not limited to, piperazinyl, pyrrolidinyl, dioxanyl, morpholinyl, and tetrahydrofuranyl, glucosyl.

Cycloalkyl, heterocycloalkyl, aryl, heteroaryl may be unsubstituted or have 1 to 4 substitutents. Examples of substituents include, but are not limited to, at least one halo, hydroxyl, amino, cyano, nitro, mercapto, carboxy, or a hydrocarbyl group selected from an alkyl, alkenyl, alkylamino, dialkylamino, or alkoxy group having one to six carbon atoms.

Exemplary hydrocarbyl-substituted cycloalkyl groups include 2-methylcyclopropyl, 2-ethylcyclopropyl, 2-methylcyclobutyl, 3-methylcyclobutyl, 2-methylcyclopentyl, 2,3-dimethylcyclopentyl, 3-iso-propylcyclopentyl, 2,6-dimethylcyclohexyl, 4-(t-butyl)cyclohexyl, 2-vinylcyclohexyl, 3-allylcyclopentyl, 3,4-diallylcyclopentyl, 1-(4-pyridinyl) piperidinyl, 1-(4-pyridinylmethyl)piperidinyl, 4-(4-pyridinyl)piperidinyl, 4-(4-pyridinyl)piperazin-1-yl, and bicyclohexyl groups.

Exemplary hydrocarbyl-substituted cyclo alkenyl groups include 3-methyl-3-cyclopenten-1-yl, 3,4-dimethyl-3-cyclopenten-1-yl, 2-iso-propyl-2-cyclopenten-1-yl, 2,3-diethyl-2-cyclopenten-1-yl, 4-vinyl-1-cyclohexen-1-yl, 3,4-diethyl-3-cyclopenten-1-yl, and 3,4-diallyl-3-cyclopenten-1-yl groups.

Exemplary hydrocarbyl-substituted aryl groups include tolyl, mesityl, xylyl, cumenyl, cymenyl, 3,5-di(t-butyl)phenyl, 2-methylnaphthyl, 2-vinylphenyl, 2-vinylbenzyl, 2-vinylnaphthyl, 4-cyclohexylphenyl, biphenyl, 4-(4-piperidinyl)pyridinyl, and p-terphenyl groups.

Exemplary hydrocarbyl-substituted heteroaryl groups include 2-methylpyridin-1-yl, 2-ethylpyridin-1-yl, 3-vinylimidazol-1-yl, 2-methylimidazol-1-yl, 2-methylquinoxalin-1-yl, 1-allylbenzotriazolyl, 2,2'-bipyridyl, 4,4'-bipyridyl, 4-methylpyrazinyl, 4-(pyridinylmethyl)-pyridinyl, 4-benzylpyrazinyl, nicotinamidyl, 2-methylfuranyl, 5-methylfurfurylamino, 2-methylthiophenyl, 4-methyloxazolyl, 2,5-diphenyl-4-methyloxazolyl, and 4-methylthiazolyl groups.

The term "halogen" denotes a chloro, fluoro, bromo or iodo substituent, preferably a chloro or fluoro substituent.

The term "optionally substituted" as used herein typically refers to substitution by Hal, —OR, —CN, —NO$_2$, —COOR, C(1-8)alkyl, C(1-8)alkylene, C(1-8)alkoxy, wherein R is from 1 to 8 carbon atoms.

In preferred embodiments, the crosslinking reagent is water soluble and biocompatible.

The term "water soluble" typically refers to a solubility of a material in water of greater than 1 wt % based on the total weight of the material and water at 24° C. It is understood that water solubility is imparted by the hydrophilic nature of the crosslinker of the invention, more specifically by the hydrophilic nature of one or more groups of A, L, X, Z, $S_1$, $S_2$, $S_3$ and $R_N$. A skilled person will know what chemical groups to select to obtain a sufficiently hydrophilic crosslinker. In preferred embodiments, the one or more of the spacer groups $S_1$, $S_2$, and $S_3$ may comprise functional groups of more hydrophilic character to increase the hydrophilicity of the resultant crosslinking reagent.

The term "biocompatible" refers to chemical inertness with respect to human cells, tissues or body fluids and minimal toxic effects of the crosslinking reagents towards such living entities.

The core structure X may be any structure which allows to build on the three branches composed of spacer groups $S_1$, $S_2$, $S_3$ and the functionalities A, L, and the aromatic hydrazine group. Thus, the core structure preferably carries three reactive functional groups as defined hereinafter, preferably carboxyl, amino, hydroxyl, thiol, or the like as attachment sites for the three spacer groups.

Typically, the core structure and spacer groups are designed such that there is negligible or no steric hindrance between the three branches (and thus between the three functionalities A, L, and the aromatic hydrazine group).

In some embodiments, the core structure X may be a substituted hydrocarbon, such as a substituted alkyl group, for example a tri- or tetra-substituted carbon atom, e.g., the α-carbon of an α-amino acid H$_2$N—CHR$_{AA}$—COOH (with R$_{AA}$ being the amino acid sidechain). Thus, X may be a natural or unnatural amino acid having a side chain R$_{AA}$ with a reactive group. Examples of natural amino acids include e.g., lysine, serine, aspartic acid, glutamic acid, cysteine, etc. Examples of unnatural amino acids include e.g. the corresponding D-amino acids, homoserine and the like). In these embodiments, the three spacer groups $S_1$, $S_2$, $S_3$ may be linked to the amino-group and the carboxy-group and the reactive side chain group $R_{AA}$.

Thus in specific embodiments, X may be a group of formula II

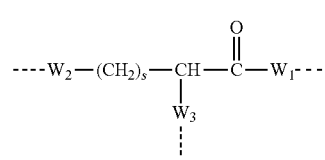

II wherein the dotted line represents the linkage of $W_1$, $W_2$, $W_3$ to groups $S_1$, $S_2$, $S_3$,
$W_1$ is —NH—, —O—, —S—, and
$W_2$, $W_3$ are independently of each other a functional group selected from —COO—, —OOC—, —CONH—, —NHCO, —NH—, —O—, —S—, and s is from 1 to 12.

In a preferred embodiment $W_1$ and $W_3$ are —NH— and $W_2$ is —CONH—

It is understood that any of the three functional groups in the group of formula IV can be coupled to any of the three linkers $S_1$, $S_2$, $S_3$. In preferred embodiments, $W_1$ is linked to $S_1$, $W_2$ is linked to $S_2$, and $W_3$ is linked to $S_3$.

Thus in other specific embodiments, the trifunctional crosslinking reagent of the invention is a compound of formula III

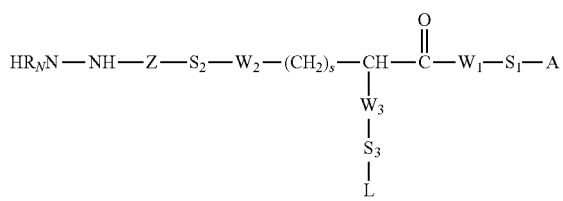

wherein
A is an affinity group;
L is a ligand-reactive group,
$S_1$, $S_2$, $S_3$ are independently of each other a spacer group;
Z is aryl or heteroaryl,
$R_N$ is H or a hydrazine-protecting group
$W_1$ is —NH—, —O—, —S—,
$W_2$, $W_3$ are independently of each other a functional group selected from —COO—, —OOC—, —CONH—, —NHCO—, —NH—, —O—, —S—, and
s is from 1 to 12.

In preferred embodiments s is methyl, ethyl, n-propyl, iso-propyl, n-butyl, iso-butyl, sec.-butyl, tert.-butyl, n-pentyl, iso-pentyl, sec.-pentyl, neo-pentyl, 1,2-dimethylpropyl, n-hexyl, iso-hexyl, n-heptyl, n-octyl.

In other embodiments, the core structure may be a substituted aryl or heteroaryl group, which is at least trisubstituted, preferably a trifunctional 6-membered aryl or heteroaryl group of formula IV

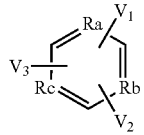

wherein $V_1$, $V_2$, $V_3$ are independently of each other a functional group such as carboxy, amine, hydroxyl, thiol and $R_a$, $R_b$, $R_c$ are independently of each other O or N.

In yet other embodiments, the core structure may be derived from a linear or cyclic glycerol or sugar moiety. A variety of sugars are available having selective (and specifically removable) protecting groups which can be used in preparation of the trifunctional crosslinking reagents described herein.

A skilled person will know that a variety of other core structures can provide the required scaffolding for the spacer groups and functionalities.

The functionality L of the trifunctional crosslinking reagent of the invention is a ligand-reactive group such as a reactive functional group or an activated functional group, which is used for coupling the spacer to a ligand of choice and thus for directing the trifunctional crosslinking reagent towards specific target glycoprotein receptors.

The term "reactive functional group" as used herein refers to an unprotected, free functional group (unless stated otherwise). In specific embodiments, a reactive functional group is selected from the group consisting of —COOH, —NH$_2$, —OH, —SH, —CH=CH— and —CH=CH—COOH.

The term "activated functional group" as used herein refers to a reactive functional group that has been activated by standard chemical techniques using a coupling agent to obtain the corresponding activated functional group. The reactive functional groups or the activated functional groups are able to react with their reactive counterpart groups present on the ligand.

The activated functional groups can be divided into subgroups according to their specific reactivity. Thus in specific embodiments, an activated functional group is selected from the group consisting of an amine-reactive group, a hydroxyl-reactive group, a thiol-reactive group, an aldehydro- or keto-reactive group, and a carboxy-reactive group.

An "amine-reactive group" is an activated functional group reacting with (primary or secondary) amines. Typical amine-reactive groups include e.g. aryl or alkyl activated carboxylic acid esters —COOR, such as N-hydroxysuccinimide esters or derivatives thereof (e.g. sulfo-N-hydroxysuccinimide esters), phenolic esters or derivatives thereof (e.g. wherein R is phenol, p-nitrophenol, tetrafluorophenol). Other amine reactive groups include acyl chlorides (—COCl), aryl and alkyl imidates —C(NH)OMe) and alkyl or aryl isocyanates —NCO or isothiocyanates —NCS.

A "hydroxyl-reactive group" is an activated functional group reacting with hydroxyls. Typical hydroxyl-reactive groups include e.g. alkyl or aryl isocyanates —NCO, and aryl or alkyl activated carboxylic acid esters —COOR.

A "thiol-reactive group" is an activated functional group reacting with thiols. Typical thiol-reactive groups include e.g. maleimides or alpha-haloamides (—NH—CO—CH$_2$-Hal).

An "aldehydro- or keto-reactive group" is an activated functional group reacting with (primary or secondary) aldehydes or ketones. Typical aldehyde- or keto-reactive groups include e.g. aryl or alkyl hydrazines (—NHNH$_2$), aryl or alkyl acylhydrazines (—CO—NHNH$_2$), alkyl or aryl hydroxylamines (—ONH$_2$).

A "carboxy-reactive group" is an activated functional group reacting with carboxylic groups. Typical carboxy-reactive group include e.g. halogen, alkyl- or arylsulfonate, hydroxyl, epoxy, mercapto, amino, isocyanato and carbodiimido groups.

Examples of activating reagents used for activating a reactive functional group include but are not limited to 1-hydroxybenzotriazole (HOBt), 3-hydroxy-3,4-dihydro-1,2,3-benzotriazine-4-one (HOOBt), N-hydroxysuccinimide (NHS), dicyclohexylcarbodiimide (DCC), diisopropylcarbodiimide (DIC), 1-ethyl-3-(3-dimethylaminopropyl)-carbodiimide (EDAC), 2-(1H-7-azabenztriazol-1-yl)-1,1,3,3-tetramethyluronium hexafluoro phosphate (HATU), 2-(1H-benzotriazol-1-yl)-1,1,3,3-tetramethyluronium hexafluorophosphate (HBTU), 3,4-dihydro-1,2,3-benzotriazin-4-one-3-oxy tetramethyluronium hexafluorophosphate (HDTU), benzotriazol-1-yloxytris(dimethylamino)phosphonium hexafluoro phosphate (BOP), benzotriazol-1-yloxytris-(pyrrolidino)-phosphonium hexafluoro phosphate (PyBop), (3,4-dihydro-1,2,3-benzotriazin-4-one-3-oxy)diethyl phosphate (DEPBt), 3,4-dihydro-1,2,3-benzotriazin-4- one-3-oxy tris-(pyrrolidino)-phosphonium hexafluorophosphate (PDOP), 2-(benzotriazol-1-yloxy)-1,3-dimethyl-2-pyrrolidin-1-yl-1,3,2-diazaphosph-olidinium hexafluorophosphonate (BOMP), 5-(1H-7-azabenzotriazol-1-yloxy)-3,4-dihydro-1-methyl 2H-pyrrolium hexachloroantimonate (AOMP), (1H-7-azabenzotriazol-1-yloxy)tris(dimethylamino)phosphonium hexafluorophosphate (AOP), 5-(1H-Benzotriazol-1-yl)-3,4-dihydro-1-methyl 2H-pyrrolium hexachloroantimonate:N-oxide (BDMP), 2-bromo-3-ethyl-4-methyl thiazolium tetrafluoroborate (BEMT), 2-bromo-1-ethyl pyridinium tetrafluoroborate (BEP), 2-bromo-1-ethyl pyridinium hexachloroantimonate (BEPH), N-(1H-benzotriazol-1-ylmethylene)-N-methyl-methanaminium hexachloroantimonate N-oxide (BOMI), N,N'-bis(2-oxo-3-oxazolidinyl)phosphinic chloride (BOP-Cl), 1-(1H-benzotriazol-1-yloxy)phenylmethylene pyrrolidinium hexachloroantimonate (BPMP), 1,1,3,3-bis(tetramethylene)fluorouronium hexafluorophosphate (BTFFH), chloro(4-morpholino)methylene morpholinium hexafluorophosphate (Cmmm), 2-chloro-1,3-dimethyl-1H-benzimidazolium hexafluorophosphate (CMBI), 2-fluoro-1-ethyl pyridinium tetrafluoroborate (FEP), 2-fluoro-1-ethyl pyridinium hexachloro antimonate (FEPH), 1-(1-pyrrolidinyl-1H-1,2,3-triazolo[4,5-b]pyridin-1-ylmethylene)pyrrolidinium hexafluorophosphate N-oxide (HAPyU), O-(1H-benzotriazol-1-yl)-N,N,N',N;-bis(pentamethylene)uronium hexafluorophosphate (HBPipU), O-(1H-benzotriazol-1-yl)-N,N,N0,N0-bis(tetramethylene)urinium hexafluorophosphate (HBPyU), (1H-7-azabenzotriazol-1-yloxy)tris(pyrrolidino)phosphonium hexafluorophosphate (PyAOP), bromotripyrrolidinophosphonium hexafluorophosphate (PyBrOp), chlorotripyrrolidinophosphonium hexafluorophosphate (PyClOP), 1,1,3,3-bis(tetramethylene)chlorouronium hexafluorophosphate (PyClU), tetramethylfluoromamidinium hexafluorophosphate (TFFH), triphosgene, triazine-based reagents [cyanuric chloride, cyanuric fluoride, 4-(4,6-dimethoxy-1,3,5-triazin-2-yl)-4-methylmorpholinium chloride (DMT-MM), 2-chloro-4,6-dimethoxy-1,3,5-triazine (CDMT)], bis(2-chlorophenyl)phosphorochloridate, diphenyl phosphorochloridate, diphenyl phosphoroazide (DPPA) and any combination thereof.

It is understood, that many pairs of ligand-reactive group and reactive group present on the ligand are feasible, and a skilled person will know which ligand-reactive group to select to couple with the ligand of choice.

In specific embodiments the activated functional group is preferably an amine-reactive group, preferably an aryl or alkyl activated carboxylic acid ester —COOR, most preferably an N-hydroxysuccinimide ester.

Thus, in a specific embodiment the trifunctional crosslinking reagent of the invention is a compound of formula V

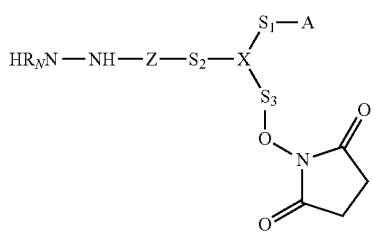

wherein X is a core structure;
$S_1$, $S_2$, $S_3$ are independently of each other a spacer group;
A is an affinity group;
Z is aryl or heteroaryl and
$R_N$ is H or a hydrazine-protecting group.

In case of core X being an α-amino acid, the trifunctional crosslinking reagent of the invention may be a compound of formula VI

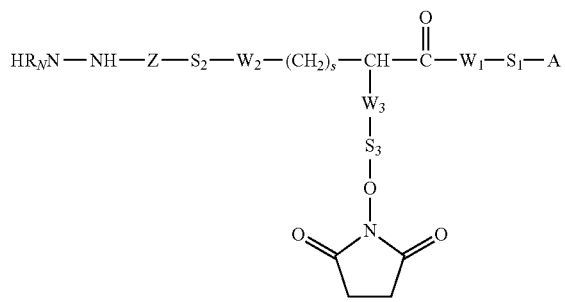

wherein
A is an affinity group;
$S_1$, $S_2$, $S_3$ are independently of each other a spacer group;
Z is aryl or heteroaryl,
$R_N$ is H or a hydrazine-protecting group
$W_1$ is —NH—, —O—, —S—,
$W_2$, $W_3$ are independently of each other a functional group selected from —COO—, —OOC—, —CONH—, —NHCO, —NH—, —O—, —S—, and
s is from 1 to 12.

The functionality A of the trifunctional crosslinking reagent of the invention is an affinity group for detection, identification and purification, preferably for affinity purification of the captured peptides.

The term "affinity group" as used herein refers to any identifiable tag, group, or moiety that is capable of being specifically bound by another composition (optionally attached or linked to a solid support, such as a bead, a filter, a plate, a membrane, a chromatographic resin, etc) for detection, identification and purification purposes. It is understood that many different species of affinity groups are known in the art and may be used, either individually or a combination of one or more different affinity groups for the present methods of the invention. Exemplary affinity groups include, but are not limited to, fluorophores, radioisotopes, chromogens, enzymes, antigens including, but not limited to, epitope tags, heavy metals, dyes, phosphorescence groups, chemiluminescent groups, electrochemical detection moieties, binding proteins, phosphors, rare earth chelates, near-infrared dyes, electrochemiluminescence groups, and the like.

Particularly suitable affinity groups for use in the trifunctional crosslinkers of the invention include affinity groups that due to a (reversible) binding affinity for a particular binding partner (typically immobilized on a solid support, such as a bead, a chromatography resin, and the like) allow the separation and isolation of the trifunctional crosslinkers (to which they have been coupled to) by means of an affinity purification method. Examples of such affinity groups include e.g. small chemical compounds (such as biotin/avidin and derivatives thereof, glutathione/GST) and short amino acid sequences, typically 2 to 20 amino acids in length, and preferably 4 to 12 amino acids in length (such as antibody fragments or the $(His)_6$ tag, $(Leu)_3$ tag, the FLAG tag or the c-Myc tag), nucleic acid sequences (e.g., DNA, RNA, or PNA), or fluorescent tags. All these affinity tags are well established in the art and commercially available. In preferred embodiments, the affinity group is selected from the group consisting of biotin and derivatives thereof, carbohydrates, and glycans, most preferred biotin and derivatives thereof.

Thus in further specific embodiments, the trifunctional crosslinking reagent of the invention is a compound of formula VII

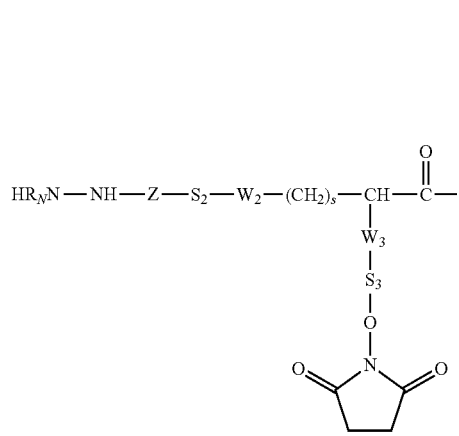

wherein
$S_1$, $S_2$, $S_3$ are independently of each other a spacer group;
$W_1$ is —NH—, —O—, —S—,
$W_2$, $W_3$ are independently of each other a functional group selected from —COO—, —OOC—, —CONH—, —NHCO—, —NH—, —O—, —S—
Z is aryl or heteroaryl,
$R_N$ is H or a hydrazine-protecting group, and
s is from 1 to 12.

Attached to the core structure are three spacer groups $S_1$, $S_2$, $S_3$ which link the core structure to the respective functionalities L, A and the aromatic hydrazine group according to a compound of formula I.

As indicated hereinabove, the three spacer groups may be chosen such that steric crowding is minimized and the reactivity of the three functionalities A, L and the aromatic hydrazine group are not compromised. Variation of linkers $S_2$ and/or $S_3$ carrying the aromatic hydrazine group and ligand-reactive group L will allow to scan the proximity of the binding site and capture different glycopeptides which may be located on the target receptor protein of interest itself or on neighboring molecules.

The term "spacer" as used herein, is typically a single bond or a straight-chain or branched, substituted or unsubstituted C(1-24)alkylene, wherein one or more, preferably non-adjacent, —CH$_2$— groups may independently from each other be replaced by one or more bridging groups and/or an unsubstituted or substituted cycloalkyl, heterocycloalkyl, aryl, heteroaryl; with the proviso that heteroatoms, such as O and N, are not directly linked to each other. A bridging group may replace a —CH$_2$— group within the alkylene chain or the terminal —CH$_2$— group.

A "bridging group" as used herein is selected from —CH(OH)—, —O—, —CO—, —CH$_2$(CO)—, —SO—, —CH$_2$(SO)—, —SO$_2$—, —CH$_2$(SO$_2$)—, —COO—, —OCO—, —S—CO—, —CO—S—, —SOO—, —OSO—, —SOS—, —O—CO—O—, —OCH$_2$—, —CH$_2$O—, —NR$_1$—, —NR$_1$—CO—, —CO—NR$_1$—, —NR$_1$—CO—O—, —O—CO—NR$_1$—, —NR$_1$—CO—NR$_1$—, —CH=CH—, —CH≡CH—, —CH=CH—COO—, —OCO—CH=CH—, —CH=N—, —C(CH$_3$)=N—, —N=N—, wherein $R_N$ represents a hydrogen atom or C(1-6)alkyl, or combinations thereof. Preferred bridging groups include —CH(OH)—, —O—, —CO—, —CH$_2$(CO)—, —COO—, —OCO—, —O—CO—O—, —OCH$_2$—, —CH$_2$O—, NR$_1$—, —NR$_1$—CO—, —CO—NR$_1$—, —NR$_1$—CO—O—, —O—CO—NR$_1$—, —NR$_1$—CO—NR$_1$—, —CH=CH—, —CH=N—, —C(CH$_3$)=N—, wherein $R_1$ represents H or C(1-6)alkyl, or combinations thereof. More preferred bridging groups include —CH(OH)—, —O—, —CO—, —CH$_2$(CO)—, —COO—, —OCO—, —O—CO—O—, —OCH$_2$—, —CH$_2$O—, NR$_1$—, —NR$_1$—CO—, —CO—NR$_1$—, wherein $R_1$ represents H or C(1-6)alkyl, or combinations thereof.

In specific embodiments, the spacer group may be a substituted or unsubstituted heteroalkylene group having 6 to 30 carbon atoms, preferably a polyethyleneglycol group (having 2 to 24 ethyleneglycol monomers in a linear configuration), a polyalcohol group, a polyamine group (e.g., spermine, spermidine and polymeric derivatives thereof), a polyester group (e.g., poly(ethyl acrylate) having from 3 to 15 ethyl acrylate monomers in a linear configuration), a polyamino acid group or a combination thereof.

More preferably, the spacer group may be a polyamino acid comprising 1 to 8 amino acids (i.e. an amino acid or a di-, tri-, tetra-, penta-, hexa-, hepta- or octapeptide) or a polyethyleneglycol group which is a di, tri-, tetra- penta- or hexaethylene glycol, or combinations of such polyamino acids and polyethyleneglyols. In preferred embodiments, the spacer groups $S_1$, $S_2$, $S_3$ represent independently from each other a linear chain comprising one or more repeating units of formula (a) and/or (b)

$$—[Y_1—(CH_2)_n]_p— \qquad (a)$$

$$—[Y_2—(CH_2)_m—Y_3]_q—, \text{or combinations thereof,} \qquad (b)$$

wherein
$Y_1$, $Y_2$, $Y_3$ are independently of each other a group selected from —O—, —CO—, COO—, —OCO—, —O—CO—O—, —OCH$_2$—, —CH$_2$O—, NR$_1$—, —NR$_1$—CO—, —CO—NR$_1$—, wherein $R_1$ represents H or C(1-6)-alkyl, and
n, m, p, and q are independently of each other an integer from 1 to 10.

Combinations of the above group (as indicated by the wording "combinations thereof") include combinations of (a) and (b) in alternating or in block form and thus may have one of the formulas

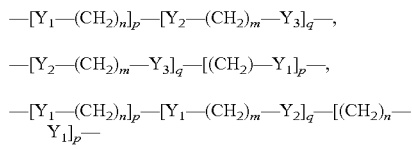

wherein $Y_1$, $Y_2$, $Y_3$ are independently of each other a group selected from —O—, —CO—, COO—, —OCO—, —O—CO—O—, —OCH$_2$—, —CH$_2$O—, NR$_1$—, —NR$_1$—CO—, —CO—NR$_1$—, wherein R$_1$ represents H or C(1-6)-alkyl, n, m, p, and q are independently of each other an integer from 1 to 10.

Thus, preferred repeating units include, but are not limited to,

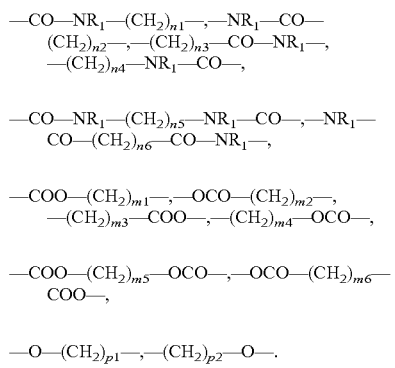

wherein R$_1$ represents H or C(1-6)-alkyl, and n1, n2, n3, n4, n5, n6, m1, m2, m3, m4, m5, m6, p1, and p2 are independently of each other an integer from 1 to 10, preferably 1, 2, 3, 4, 5, or 6.

Other combinations of the above groups may also include combinations of various repeating units (a), for example having the following formula

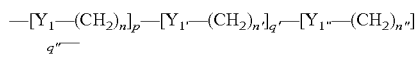

wherein $Y_1$, $Y_{1'}$, $Y_{1''}$ are independently of each other a group selected from —O—, —CO—, COO—, —OCO—, —O—CO—O—, —OCH$_2$—, —CH$_2$O—, NR$_1$—, —NR$_1$—CO—, —CO—NR$_1$—, wherein R$_1$ represents H or C(1-6)-alkyl, and n, n', n" are independently of each other an integer from 1 to 10.

Thus in specific embodiments the invention is directed to compounds of formulas I, III, IV, V, VI, VII wherein A is an affinity group, Z is aryl or heteroaryl, $S_1$, $S_2$, $S_3$ are independently from each other a linear chain comprising at least one repeating unit of formula (a) —[Y$_1$—(CH$_2$)$_n$]$_p$—, (b) —[Y$_2$—(CH$_2$)$_m$—Y$_3$]$_q$— or combinations thereof, wherein $Y_1$, $Y_2$, $Y_3$ are independently of each other a group selected from —O—, —CO—, COO—, —OCO—, —O—CO—O—, —OCH$_2$—, —CH$_2$O—, NR$_1$—, —NR$_1$—CO—, —CO—NR$_1$—, wherein R$_1$ represents H or C(1-6)-alkyl, and n, m, p, and q are independently of each other an integer from 1 to 10.

In a most preferred embodiment the invention is directed to a trifunctional crosslinking reagent of formula VIII

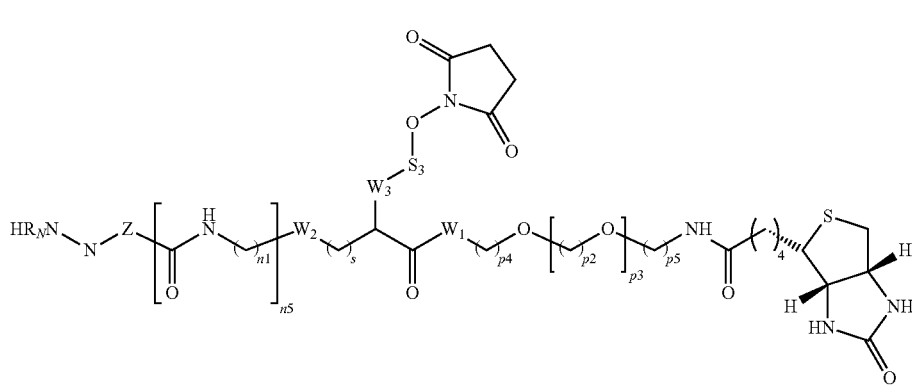

wherein $W_1$ is —NH—, —O—, —S—, $W_2$, $W_3$ are independently of each other a functional group selected from —COO—, —OOC—, —CONH—, —NHCO, —NH—, —O—, —S—, Z is aryl or heteroaryl, $R_N$ is H or a hydrazine-protecting group, n1, n5, p2, p3, p4, p5, s are independently of each other 1, 2, 3, 4, 5 or 6.

It is understood that for use in the preparation of the trifunctional crosslinkers of the invention, the spacer group is preferably provided with terminal functional groups which can be selectively protected or activated for attachment to X or one of the functionalities A, L and the aromatic hydrazine group. Thus, in some embodiments, the spacer groups may be coupled to X and the respective functionality (A, L or the aromatic hydrazine group) through a bridging group, preferably through groups selected from —COO—, —CO—NR$_1$—, —O—, —NR$_1$—, —NR$_1$—COO—, and —S—S— linkages. It is further understood that there is no preferred order of assembling core structure, spacer and one of the three functionalities A, L and aromatic hydrazine group. A skilled person will know that depending on the nature of the various groups one order of assembly may be preferred.

A further functionality of the trifunctional crosslinking reagent of the invention is the protected or unprotected aromatic hydrazine group, which is (in its unprotected form) capable of selectively forming a covalent bond with oxidized carbohydrate groups of glycopeptides on a cell surface or secreted glycoprotein. Said oxidized glycopeptides may be located on the cell surface or secreted glycoprotein itself or else may be located on spatially close molecules that interact with the target glycoprotein receptor. The lengths of the spacers $S_2$ and $S_3$ determine the distance between ligand binding site and said oxidized glycopeptide. Thus, varying the lengths of spacers $S_2$ and $S_3$ allows to scan or probe the immediate or expanded environment of the ligand binding site.

substituted pyridyl, furyl, imidazolyl, benzimidazolyl, pyrimidinyl, thienyl, quinolinyl, indolyl, and thiazolyl, preferably pyridyl, furyl, imidazolyl, benzimidazolyl, pyrimidinyl, nicotinamidyl.

Thus the protected aromatic hydrazine group, is preferably a trifluoroacetyl-protected heteroaryl-hydrazine, more preferably a trifluoroacetyl nicotinamido hydrazine group.

Most preferably the compound of formula I may be a trifunctional crosslinker reagent of formula IX

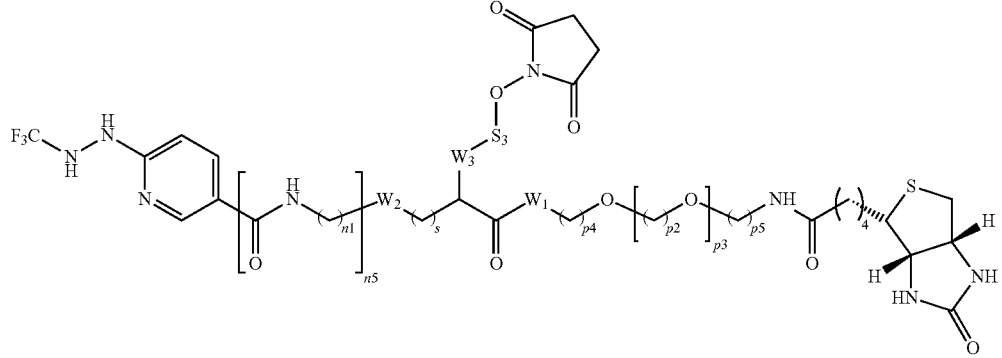

IX

The aromatic hydrazine group may be protected or unprotected. Generally, any amine protecting group can also be used for protecting hydrazine groups, and conditions which are suitable for protecting and deprotecting amines with these protecting groups are also suitable for use with hydrazines. Protecting groups for amines and conditions for protecting and deprotecting amines with these protecting groups are known in the art and are disclosed, for example, in Greene and Wuts, "Protective Groups in Organic Synthesis", John Wiley & Sons (1991). Specific examples of suitable hydrazine protecting groups are hydrazones (R'R''C=NNH$_2$) which can be aldehyde or ketone hydrazones having substituents selected from hydrogen, substituted (C1-C6)alkyl, substituted aryl and substituted heteroaryl. It is understood that the choice of a protecting group for use in the present invention may depend on the intended use of the crosslinking reagent. Suitable protecting groups for use of the crosslinker to target cell surface glycoproteins on live cells or to target secreted glycoproteins should be amenable to in situ displacement, i.e. they should protect the hydrazine group as long as possible to avoid any side reactions, and should be removable under mild conditions, e.g. in vivo- or under protein-compatible conditions. It is further understood that for other applications (e.g. in vitro), the hydrazines may also bear a protecting group which may be displaced prior to the use of the trifunctional crosslinker as glycopeptide capturing agent.

Preferred hydrazine protecting groups include, but are not limited to, trifluoroacetyl, tert-butoxycarbonyl (Boc), benzyloxycarbonyl (Cbz) and fluorenylmethyloxycarbonyl (Fmoc), sulfmoc (Fmoc-SO$_3$H), more preferably trifluoroacetyl.

Thus, in a more preferred embodiment, the invention is directed towards a compound of formula I, III, V, VI, VI, wherein $R_N$ is trifluoroacetyl.

In other embodiments, Z is an aryl group selected from unsubstituted or substituted phenyl, naphthyl, and anthracenyl or a heteroaryl group selected from unsubstituted or wherein
$W_1$ is —NH—, —O—, —S—,
$W_2$, $W_3$ are independently of each other a functional group selected from —COO—, —OOC—, —CONH—, —NHCO, —NH—, —O—, —S—,
n1, n5, p2, p3, p4, p5, s are independently of each other 1, 2, 3, 4, 5 or 6

In a further aspect, the invention is directed to the use of the trifunctional crosslinking reagents of the invention for characterizing and analyzing ligand-target glycoprotein receptor interactions.

Briefly, as shown above, the crosslinkers of the invention combine two different chemically reactive groups and an affinity group in a trifunctional molecule. The first chemically reactive group is a ligand-reactive group, preferably a N-hydroxysuccinimide, used for coupling of the crosslinker to a ligand of interest, which is then binding to a (cell-surface or secreted) target glycoprotein receptor of interest. The second chemically reactive group is an aromatic hydrazine, preferably a trifluoroacetylated aromatic hydrazine, for capturing oxidized receptor glycopeptides. Conjugated to a ligand of interest, the affinity-tagged crosslinkers of the invention allow for the carbohydrate-directed capturing of interacting target glycoprotein receptors on oxidized live cells or in solution and the subsequent two-step affinity purification of captured glycopeptides through the affinity group, preferably biotin, for subsequent mass spectrometric analysis. Through the quantitative comparison with an undirected control sample, affinity tagging events (e.g. biotinylations) originating from interactions of ligands with their corresponding target glycoprotein receptors can clearly be distinguished from unspecific, stochastic affinity tagging events (e.g. biotinylations) of random (cell surface or secreted) proteins. This allows for the detection of even low-affinity and transient ligand-target glycoprotein receptor interactions as well as off-target effects of ligands with low-abundant glycoproteins that are present in membrane-bound form in their original cellular environment or in secreted form in a biological fluid.

This is illustrated schematically in FIG. 1 in the case of cell surface target glycoprotein receptors: The ligand of interest (illustrated by filled circles) is coupled with a trifunctional crosslinker in a protein compatible buffer solution. In a separate control reaction, an equimolar amount of crosslinker is coupled to a control protein or quenched in pure buffer solution (FIG. 1A). In order to generate aldehyde groups on cell surface carbohydrates, live cells are oxidized (FIG. 1B). The previously coupled ligands are then added to the oxidized cells to allow for the capturing of oxidized cell surface glycostructures (step 2 and FIG. 1C). Thereby, random cell surface glycoproteins are labeled through stochastic events and target cell surface glycoprotein receptors for the ligand of interest are captured more efficiently through direct ligand-receptor interactions. In parallel, the control probe is added to an equal number of cells resulting in stochastic labeling events only. For all the following steps, both probes are processed in parallel. After the labeling reactions, cells are lysed and the nuclear fraction is discarded (step 3). The remaining fractions are deterged, reduced, alkylated and subsequently digested with trypsin (step 3, FIG. 1D). After a complete digest of the probes, biotinylated cell surface glycopeptides are affinity purified on streptavidin beads through extensive washing with a variety of buffers (step 4, FIG. 1E). After washing, N-glycopeptides are specifically released from the beads through an enzymatic step with PNGase F, which cleaves between the innermost component of the oligosaccharide structure and the asparagine of the glycopeptide in the N-X-S/T glycosylation motif of the peptide (wherein N stands for asparagine, X stands for any amino acid except proline, and S/T for serine or threonine, respectively). By doing so, PNGaseF deamidates the asparagine and introduces the specific N115-X-S/T signature in formerly glycosylated peptides (step 5, FIG. 1F). The released peptides are desalted and resuspended in a suitable buffer solution for the analysis with a high mass accuracy mass spectrometer. For the analysis, mass spectrometers are operated in the data dependent mode in which ion signals above a predetermined threshold automatically trigger the instrument to switch from MS to MS/MS mode for generating collision-induced dissociation (CID) spectra of peptides (step 6, FIG. 1G). All MS/MS spectra are searched against a standard protein database and the identified peptides are filtered for the presence of the N115-X-S/T motif (step 7, FIG. 1H). The concentration of cell surface peptides in the ligand sample is quantitatively compared to the control sample in order to detect specific enrichments of cell surface receptors. For stochastically tagged peptides from cell surface proteins, ratios should be around 1 and glycoprotein receptor peptides that are specifically captured in a ligand-based fashion get higher values in the ligand sample vs. control. If proteins are identified with more than one peptide, the abundance information can be combined (step 8, Figure H).

Thus, in a further aspect, the present invention is directed towards a method of identifying specific interactions between a ligand and a target glycoprotein receptor having at least one carbohydrate residue in a sample, wherein the ligand recognizes a ligand-specific peptide domain on the target glycoprotein receptor, comprising the steps of:
i) providing a sample comprising said target glycoprotein receptor,
ii) subjecting the target glycoprotein receptor to oxidative treatment to generate aldehyde functions on the at least one carbohydrate residue thereby obtaining an oxidized target glycoprotein receptor,
iii) providing a trifunctional crosslinking reagent of formula I according to claim 1,

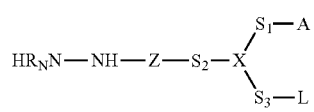

wherein X is a core structure; $S_1$, $S_2$, $S_3$ are independently of each other a spacer group; L is a ligand-reactive group; A is an affinity group; Z is aryl or heteroaryl and $R_N$ is a hydrazine-protecting group, and allowing the ligand-reactive group to conjugate to said ligand to obtain a ligand-crosslinking reagent-complex,
iv) contacting the sample with the ligand-crosslinking reagent-complex under conditions under which (a) the ligand is able to bind to the ligand-specific protein domain on the target glycoprotein receptor and (b) the protected hydrazine group is converted to its free form and allowed to react with the oxidized target glycoprotein receptor, to obtain a dual peptide-bound complex,
v) isolating and purifying the dual peptide-bound complex from the sample,
vi) releasing the peptides from the purified dual peptide-bound complex obtained in step (iv) to obtain released peptides and
vii) analyzing and quantifying the released peptides obtained in step (v) by high mass accuracy mass spectrometry, and
viii) identifying the interactions between the ligand and the target glycoprotein receptor through quantitative comparison to an undirected control reaction.

As indicated above, it is understood, that the target glycoprotein receptor may be either in solution or on the surface of a cell.

Specific embodiments of the core structure X; the spacer groups $S_1$, $S_2$, $S_3$; the ligand-reactive group L; the affinity group A; the hydrazine-protecting group $R_N$ as well as the (hetero) aryl Z are as defined hereinbefore. Thus in preferred embodiments the above method of the invention is carried out using a compound of formula III, V, VI, VII, VIII or IX.

Thus in some embodiments, the present invention is directed towards a method of identifying specific interactions between a ligand and a cell surface receptor having at least one carbohydrate residue in a sample comprising a population of cells, wherein the ligand recognizes a ligand-specific peptide domain on the target glycoprotein receptor, comprising the steps of:
i) providing a sample comprising a population of cells, one or more of which expresses at least one glycoprotein receptor,
ii) subjecting the cell surface receptor to oxidative treatment to generate aldehyde functions on the at least one carbohydrate residue thereby obtaining an oxidized cell surface receptor,
iii) providing a trifunctional crosslinking reagent of the invention, more specifically a trifunctional crosslinking reagent of formula I, III, V, VI, VII, VIII or IX, and allowing the reagent to conjugate to said ligand to obtain a ligand-crosslinking reagent-complex,
iv) contacting the sample with the ligand-crosslinking reagent-complex under conditions under which (a) the ligand is able to bind to the ligand-specific peptide domain on the cell surface receptor and (b) the protected hydrazine group is converted to its free form and allowed to react with the oxidized cell surface receptor, to obtain a dual peptide-bound complex v) isolating and purifying the dual peptide-bound complex from the sample, vi) releasing the peptides from the purified dual peptide-bound complex obtained in step (iv) to obtain released peptides and vii) analyzing and quantifying the released peptides obtained in step (v) by high mass accuracy mass spectrometry, and viii) identifying the interactions between the ligand and the cell surface receptor through quantitative comparison to a control reaction.

In other embodiments, the present invention is directed towards a method of identifying specific interactions between a ligand and a secreted glycoprotein receptor having at least one carbohydrate residue contained in a biological fluid, wherein the ligand recognizes a ligand-specific peptide domain on the secreted glycoprotein receptor comprising the steps of:

i) providing a concentrated sample from the biological fluid containing the secreted glycoprotein receptor ii) subjecting the secreted glycoprotein receptor to oxidative treatment to generate aldehyde functions on the at least one carbohydrate residue thereby obtaining an oxidized secreted glycoprotein receptor, iii) providing a trifunctional crosslinking reagent of the invention, more specifically a trifunctional crosslinking reagent of formula I, III, V, VI, VII, VIII or IX, and allowing the reagent to conjugate to said ligand to obtain a ligand-crosslinking reagent-complex, iv) contacting the sample with the ligand-crosslinking reagent-complex under conditions under which (a) the ligand is able to bind to the ligand-specific peptide domain on the secreted glycoprotein receptor, and (b) the protected hydrazine group is converted to its free form and allowed to react with the oxidized secreted glycoprotein receptor to obtain a dual peptide-bound complex v) isolating and purifying the dual peptide-bound complex from the sample, vi) releasing the peptides from the purified dual peptide-bound complex obtained in step (iv) to obtain released peptides and vii) analyzing and quantifying the released peptides obtained in step (v) by high mass accuracy mass spectrometry, and viii) identifying the interactions between the ligand and the secreted glycoprotein receptor through quantitative comparison to a control reaction.

In other preferred embodiments the ligand-reactive group is preferably an activated functional group, more preferably an amine-reactive group, most preferably an N-hydroxysuccinimide group or an N-hydroxysulfosuccinimide group (with increased water solubility).

The term "sample" or "biological sample", as used herein, refers to any solid or fluid sample obtained from, excreted by or secreted by any living cell or organism, including, but not limited to, tissue culture, bioreactors, human or animal tissue, plants, fruits, vegetables, single-celled microorganisms (such as bacteria and yeasts) and multicellular organisms. For example, a biological sample can be a biological fluid obtained from, e.g., blood, plasma, serum, urine, bile, seminal fluid, cerebrospinal fluid, aqueous or vitreous humor, or any bodily secretion, a transudate, an exudate (e.g., fluid obtained from an abscess or any other site of infection or inflammation), or fluid obtained from a joint (e.g., a normal joint or a joint affected by disease such as a rheumatoid arthritis, osteoarthritis, gout or septic arthritis). A biological sample can also be, e.g., a sample obtained from any organ or tissue (including a biopsy or autopsy specimen), can comprise cells (whether primary cells or cultured cells), medium conditioned by any cell, tissue or organ, tissue culture.

The term "glycoprotein" (or "glycopeptides") as used herein refers to a protein (or peptide) that contains one or more covalently linked carbohydrate or oligosaccharide groups. The carbohydrate groups are typically attached through an amine side chain group, typically of the asparagine amino acid (to give N-linked carbohydrates) or through a hydroxyl side chain group, usually of the serine or threonine amino acids (to give O-linked carbohydrates). An oxidized glycoprotein or glycopeptide refers to a glycoprotein or glycopeptide, which has undergone treatment with a suitable oxidizing reagent thereby cleaving vicinal diol moieties of the attached carbohydrate to yield aldehyde groups. Such an oxidation of carbohydrates (to give dialdehyde carbohydrates) may be carried out according to conventional procedures e.g. using periodic acid or periodate salts, lead(IV) salts or permanganate, preferably sodium (meta)periodate. Alternatively, chemical approaches can exploit metabolic labeling of cells using analogs of glycan precursors that carry bioorthogonal groups (such as azide, alkyne, ketone or aldehyde) to generate attachment sites for the crosslinkers on glycoprotein receptors (Current opinion in chemical biology (2007) vol. 11 (1) pp. 52-8)

The terms "protein", "polypeptide", "oligopeptide" and "peptide" as used herein have the same meaning and refer to an amino acid polymer having any length (typically a peptide is referred to as a fragment of a protein). This polymer may be a straight, branched or cyclic chain. An amino acid may be a naturally-occurring or nonnaturally-occurring amino acid, or a variant amino acid. The term "fragment" with respect to a polypeptide or polynucleotide refers to a polypeptide or polynucleotide having a sequence length ranging from 1 to n−1 with respect to the full length of the reference polypeptide or polynucleotide (of length n). The length of the fragment can be appropriately changed depending on the purpose.

For the present invention a glycoprotein may be a glycoprotein that occurs in nature, or may alternatively have a sequence that was engineered synthetically (with the proviso that an engineered glycoprotein contains at least one peptide sequence that serves as a glycosylation site). A glycoprotein may be an intracellular glycoprotein, a cell surface glycoprotein (i.e. a glycoprotein bound to the surface of a cell) or a glycoprotein in solution (i.e. a glycoprotein secreted into the medium).

A glycoprotein for use in the methods of the present invention may be any pharmaceutically or commercially relevant glycoprotein with an interesting or useful biological or chemical activity, such as a receptor, antibody, enzyme, hormone, regulatory factor, antigen, binding agent etc. The following list of glycoproteins that may be used in the methods of the present invention is merely exemplary and is not intended to be a limiting recitation. A skilled person will understand that any glycoprotein may be used in the present methods and will be able to select the particular glycoprotein based on his or her particular needs.

The term "target glycoprotein receptor" or "glycoprotein receptor" refers to a glycoprotein to which one or more specific kinds of ligands or signaling molecules may bind. Such a (target) glycoprotein receptor may be present in a biological fluid or on cells derived from any subject, preferably a mammalian subject, e.g. a human or animal. Thus, when used in combination with the term "cell surface" (i.e. cell-surface glycoprotein receptor) it refers to a glycoprotein being associated with the plasma membrane of a cell, to which one or more specific kinds of ligands or signaling molecules may bind. When used in combination with the term "oxidized" it refers to a glycoprotein whose carbohydrate portions have been oxidized to form aldehyde groups by a suitable oxidative treatment.

Glycoprotein receptors include any cell-surface receptors or any secreted receptors, such as those disclosed in Varki, A. et al. Essentials of Glycobiology, Cold Spring Harbor Laboratory Press, 2009 and www.uniprot.org. Non-limiting examples of glycoprotein receptors include for example receptors comprising Fibroblast Growth Factor Receptor 1 (FGFR1) (Swiss-Prot Ass. Nos: Q9QZM7, Q99AW7, Q9UD50, Q63827), Fibroblast Growth Factor Receptor 2 (FGFR2) (Swiss-Prot Ass. Nos: Q96KM2, P21802, Q63241), Fibroblast Growth Factor Receptor 3 (FGFR3) (Swiss-Prot Ass. Nos: Q95M13, AF487554, Q99052), Fibroblast Growth Factor Receptor 4 (FGFR4) (Swiss-Prot Ass. No: Q91742), Neurotrophin Tyrosin Kinase Type-2 (NTRKT-2) (Swiss-Prot Ass. No: Q8WXJ5), Leukocyte Antigen Related Protein-Tyrosine Phosphatase (LAR-PT-PRF) (Swiss-Prot Ass. Nos: Q9EQ17, Q64605, Q64604, Q9QW67, Q9VIS8 P10586), Nephrin (Swiss-Prot Ass. Nos: Q925S5, Q9JIX2, Q9ET59, Q9R044, Q9QZS7, Q06500), Protein-Tyrosine Phosphatase Receptor type S (PTPRS) (Swiss-Prot Ass. Nos: Q64699, Q13332, O75870), Protein-Tyrosine Phosphatase Receptor type kappa (R-PTP-kappa) (Swiss-Prot Ass. No: Q15262), Protein-Tyrosine Phosphatase Receptor type D (PTPRD) (Swiss-Prot Ass. Nos: QBWX65, Q9IAJ1, P23468, Q64487), Ephrin type-A receptor 8 (EPHA8/Tyrosine-Protein Kinase Receptor EEK) (Swiss-Prot Ass. Nos: O09127, P29322), Ephrin type-A receptor 3 (EPHA8/Tyrosine-Protein Kinase Receptor ETK-1/GEK4) (Swiss-Prot Ass. No: P29318), Ephrin type-A receptor 2 (Swiss-Prot Ass. No: Q8N3Z2), Insulin Receptor (IR) (Swiss-Prot Ass. No: Q9PWN6), Insulin-like Growth Factor-1 Receptor (IGF-1) (Swiss-Prot Ass. Nos: Q9QVW4, P08069, P24062, Q60751, P15127, P15208), Insulin-related Receptor (IRR) (Swiss-Prot Ass. No: P14616), Tyrosine-Protein Kinase Receptor Tie-1 (Swiss-Prot Ass. Nos: 06805, P35590, Q06806), Roundabout receptor-1 (robo-1) (Swiss-Prot Ass. Nos: O44924, AF041082, Q9Y6N7), Neuronal nicotinic acetylcholine receptor alpha 3 subunit (CHRNA3) (Swiss-Prot Ass. Nos: Q8VHH6, P04757, Q8R4G9, P32297), Neuronal acetylcholine receptor alpha 6 subunit (Swiss-Prot Ass. Nos: Q15825, Q9R0W9) Platelet-Derived Growth Factor Receptor Beta (PDGFRB) (Swiss-Prot Ass. Nos: Q8R406, Q05030), Interleukin-6 Receptor (IL-6R) (Swiss-Prot Ass. No: Q00560), Interleukin-23 Receptor (IL-23R) (Swiss-Prot Ass. No: AF461422), Beta-common cytokine receptor of IL-3, IL5 and GmCsf (Swiss-Prot Ass. No: P32927), Cytokine Receptor-Like molecule 3 (CRLF1) (Swiss-Prot Ass. No: Q9JM58), Class I Cytokine Receptor (ZCYTOR5) (Swiss-Prot Ass. No: Q9UHH5), Netrin-1 receptor DCC (Swiss-Prot Ass. No: P43146), Leukocyte Fc Receptor-like Protein (IFGP2) (Swiss-Prot Ass. Nos: Q96PJ6, Q96KM2), Macrophage Scavenger Receptor 2 (MSR2) (Swiss-Prot Ass. No: Q91YK7), or Granulocyte Colony Stimulating Factor Receptor (G-CSF-R) (Swiss-Prot Ass. No: Q99062), or fragments, or variants thereof.

In other embodiments the glycoprotein receptor is selected from the group of proteoglycans. More preferably the proteoglycan is selected from the group comprising heparan sulphate proteoglycans. In the most preferred embodiment the proteoglycan is perlecan (Swiss-Prot Ass. No: P98160), or a fragment, or a variant thereof.

In yet other embodiments the glycoprotein receptor is a receptor selected from the group of membrane-anchored cell-surface enzymes. For example the cell-surface receptor is selected from the group comprising the pitrilysin family of metalloproteinases or the family of desintegrin and metalloproteases (ADAMs) comprising ADAM-8 (Swiss-Prot Ass. No: Q05910), ADAM-19 (Swiss-Prot Ass. Nos: Q9H013, O35674), ADAM-8 (Swiss-Prot Ass. No: P78325), ADAM-12 (Swiss-Prot Ass. Nos: O43184, Q61824), ADAM-28 (Swiss-Prot Ass. Nos: Q9JLN6, Q61824, Q9XSL6, Q9UKQ2), ADAM-33 precursor (Swiss-Prot Ass. Nos: Q8R533, Q923W9), ADAM-9 (Swiss-Prot Ass. Nos: Q13433, Q61072), ADAM-7 (Swiss-Prot Ass. Nos: Q9H2U9, O35227, Q63180), ADAM-1A Fertilin alpha (Swiss-Prot Ass. No: Q8R533), ADAM-15 (Swiss-Prot Ass. Nos: Q9QYV0, O88839, Q13444), Metalloproteinase-desintegrin domain containing protein (TECAM) (Swiss-Prot Ass. No: AF163291), Metalloproteinase 1 (Swiss-Prot Ass. Nos: O95204, Q9BSI6), or fragments, or variants thereof.

In some embodiments, the glycoprotein receptor may be an enzyme, such as, for example, hydrolases, transferases, isomerases, lyases, ligases, transferases and oxidoreductases. Examples of hydrolases include lipase, cholinesterase, alkaline phosphatase, β-amylase deoxyribonuclease, glucoamylase A and B, α-galactosidase I and II, β-fructofuranosidase, β-glucouronidase, N-acetyl-β-glucosaminidase, hyaluronidase, oxytocinase, kallikrein, bromelain, enterokinase, proteinase a, b, and c, pepsinogen and pepsin. Examples of oxidoreductases include glucose oxidase, peroxidase and chloroperoxidase. Examples of transferases include γ-glutamyltranspeptidase and ribonuclease. A skilled person will be aware of other known examples of enzymes that can be used in accordance with the methods of the present invention.

In further embodiments a glycoprotein receptor may be a growth factor or other signaling molecule. Growth factors are typically glycoproteins that are secreted by cells and bind to and activate receptors on other cells, initiating a metabolic or developmental change in the receptor cell. Non-limiting examples of mammalian growth factors and other signaling molecules include cytokines; epidermal growth factor (EGF); platelet-derived growth factor (PDGF); fibroblast growth factors (FGFs) such as FGF-5; insulin-like growth factor-T and -II (IGF-I and IGF-II); des(1-3)-IGF-I (brain IGF-I), insulin-like growth factor binding proteins; CD proteins such as CD-3, CD-4, CD-8, and CD-I 9; erythropoietin; osteoinductive factors; immunotoxins; bone morphogenetic proteins (BMPs); interferons such as interferon-alpha, -beta, and -gamma; colony stimulating factors (CSFs), e.g., M-CSF, GM-CSF, and G-CSF; most interleukins; tumor necrosis factor (TNF) beta; follicle stimulating hormone; calcitonin; luteinizing hormone; anti-clotting factors such as Protein C; atrial natriuretic factor; lung surfactant; plasminogen activators, such as urokinase or human urine or tissue-type plasminogen activator (t-PA); hematopoietic growth factor; and enkephalinase. One of ordinary skill in the art will be aware of other growth factors or signaling molecules that can be used in accordance with the methods of the present invention.

The term "ligand" specific for a particular target glycoprotein receptor is used broadly herein and refers to any compound which is able to interact or bind with a target glycoprotein receptor which is membrane-bound and located on a cell surface or in a secreted form. Each target glycoprotein receptor may have one or more specific ligand binding sites, which can be the same or different or overlapping for different ligands, and which are specific peptide domains within the whole target glycoprotein receptor (i.e. a specific portion of the protein) where ligand binding occurs. Recognition between ligand and peptide domain may be due to sequence specificity, three-dimensional structure, or post-translational modifications of the ligand or the target glycoprotein receptor. Examples of a ligand include, without limitation, a peptide, including a glycopeptide, a polypeptide, protein, including a glycoprotein or phosphoprotein, a carbohydrate, glycolipid, phospholipid, oligonucleotide, polynucleotide, aptamers, vitamin, antigens and fragments thereof, haptens, receptor agonists, partial agonists, mixed agonists, antagonists, drugs, chemokines, hormones (e.g. LH, FSH, TRH, TSH, ACTH, CRH, PRH, MRH, MSH, glucagon and prolactin; transferrin; lactoferrin; angiotensin; histamine; insulin; lectins), transmitters, autocoids; growth factors (for example PDGF, VEGF, EGF, TGFa, TBFβ, GM-CSF, G-CSF, M-CSF, FGF, IGF, bombesins, thrombopoietin, erythropoietin, oncostatin and endothelin 1), cytokines including interleukins (e.g. interleukins 1 to 15), lymphokines and cell signal molecules, such as tumor necrosis factor (e.g. tumour necrosis factors α and β) and interferons (e.g. interferons α, β and γ), prosthetic groups, coenzymes, cofactors, regulatory factors, or any other naturally occurring or synthetic organic molecule which can specifically bind to a receptor, including fragments, analogs and other derivatives thereof that retain the same binding properties. A ligand specific for a particular cell surface target glycoprotein receptor may be targeting a wide range of cell types or a specific cell type.

In some embodiments a ligand is selected from the group comprising peptides, carbohydrates, lipids or nucleotides. The term nucleotide includes natural nucleotides, nucleotide analogues, nucleotide derivatives, di-, oligo- or polynucleotides, or nucleotide comprising substances. A nucleotide analogue is defined as a molecule comprising a nucleotide base or a modified nucleotide base, a sugar residue or a modified sugar residue and a mono-, di-, tri-, quadra-, or penta-ester group. If a fragment of for example a protein is used, i.e. a peptide, it may be of any suitable length. It is understood, that the (minimal) length and composition of the peptide, i.e. the number and type of amino acids, is dictated by the nature of the binding interaction. A peptide may typically comprise for example from 3-100 amino acid residues.

In some embodiments, the ligand may be an antibody. Antibodies are heavy (~150 kDa) globular plasma proteins with oligosaccharide chains added to some of their amino acid residues. They have the ability to specifically bind a particular antigen. Given the large number of antibodies currently in use or under investigation as pharmaceutical or other commercial agents, analysis of the binding interactions with a particular ligand in accordance with the methods of the present invention is of particular interest. In some embodiments, an antibody may be a monoclonal antibody such as the therapeutic antibodies Trastuzumab and Bevacizumab. In some embodiments, a monoclonal antibody is a humanized antibody. In other embodiments, an antibody can be polyclonal.

In some embodiments, engineered affinity binders can be employed such as ankyrin repeat binders, affinity binders generated by phage display, or oligonucleic acid or peptide aptamers.

In some embodiments, the ligand may be a glycoprotein such as the glycoprotein receptors mentioned hereinabove. In some embodiments, the ligand may be a domain of a cell-surface protein such as the cell-surface glycoprotein receptors mentioned hereinabove.

According to the invention a ligand interacts with its target glycoprotein receptor through its binding site, which is a specific peptide fragment of a target glycoprotein receptor, such as a particular amino acid sequence or the three-dimensional structure of that fragment of a target glycoprotein receptor which is referred to as the binding site. The term "interact" or "interaction" with reference to a ligand binding to its (cell-surface or secreted) target glycoprotein receptor binding site includes a transient or permanent direct or indirect contact between the (cell-surface or secreted) target glycoprotein receptor and the ligand and may be characterized by its binding affinity, i.e. its dissociation equilibrium constant $K_d$. Typical binding affinities of a ligand for its target glycoprotein receptor may be at least $10^{-5}$M, preferably $10^{-7}$ M and greater, e.g. around $10^{-8}$ M to around $10^{-12}$ M. The methods of the present invention allow the detection of both typical binding affinities as well as lower affinity interactions between a (cell-surface or secreted) target glycoprotein receptor and a ligand characterized by $K_d$ having e.g. a value of less than $10^{-5}$ M.

Thus, in a typical method of the invention the following steps are performed:

In a first step, the ligand-reactive group of the crosslinker of the invention, preferably an activated functional group, more preferably an N-hydroxysuccinimide group, enables the efficient coupling to ligands via primary amines under protein compatible conditions and without loss of the hydrazine function to obtain a ligand-crosslinker complex. In a separate control reaction, an equimolar amount of crosslinker is coupled to a control protein or incubated in pure buffer solution for hydrolysis of the activated functional group, e.g. the NHS ester.

In a second step, the ligand-crosslinker complex is added to a sample comprising either cell(s), tissue(s), or solution(s) comprising a target glycoprotein receptor, which have been subjected to oxidative treatment using e.g. periodate (e.g. 1-2 mM NaIO$_4$) to generate aldehyde groups on the carbohydrates present on the target glycoprotein receptors, under conditions that allow the ligand within the ligand-crosslinker complex to bind to its specific binding site.

In case of cell surface glycoprotein receptors as defined hereinabove, the sample comprises a population of cells of which at least one expresses such a cell surface glycoprotein receptor. In case of secreted glycoproteins as defined hereinabove, the sample comprises a biological fluid comprising at least one secreted glycoprotein.

Thus, in a specific embodiment of the method of the invention, the oxidized glycopeptide referred to in step (iii) of the above disclosed method is obtained by subjecting the sample comprising the population of target glycoprotein receptors (according to step (i)) to oxidative treatment prior to contacting the sample with the ligand-crosslinking reagent-complex (according to step (iii)), to oxidize the carbohydrates present on the receptor peptide side chains. Upon ligand binding, the hydrazine group will react (in its unprotected form) with these oxidized sites. The oxidation of a carbohydrate structure on a glycopeptide usually generates several potential oxidized attachment sites, yet the glycopeptides captured by the hydrazine group of the ligand-crosslinking reagent-complex remain the same.

Thus, step (i) of the above method preferably includes (a) providing a sample comprising at least one target glycoprotein receptor in secreted form or on a cell surface, and (b) subjecting the sample to oxidative treatment to obtain a sample comprising at least one oxidized target glycoprotein receptor, i.e. at least one target glycoprotein receptor carrying at least one oxidized carbohydrate group.

In a third step, the sample is subjected to conditions such that the protecting group of the hydrazine may be removed. If the trifluoroacetyl group is used as protecting group for the aromatic hydrazine, then the conditions for oxidizing the carbohydrates also effects its removal and the free hydrazine may efficiently capture the aldehyde groups of the oxidized glycopeptides. While random glycoproteins are captured through stochastic events, aldehyde groups in proximity to the ligand binding site on the receptors are captured more efficiently due to local enrichment caused by the direct ligand-target glycoprotein receptor interactions. This dual labeling event per tri functional crosslinking reagent results in a dual peptide-bound complex. In analogy, a control probe (such as the quenched crosslinker, or the crosslinker conjugated with an unspecific molecule, or the crosslinker conjugated with a ligand molecule with a distinct receptor specificity) is added to an equal number of cells resulting in stochastic labeling events only (for all the following steps, the control probe may be processed in parallel).

In a fourth step, the sample is processed and subjected to enzymatic digestion according to standard procedures (Wollscheid et al. Nat Biotech (2009) vol. 27 (4) pp. 378-86).

In case of a method of identifying specific interactions between a ligand and a target glycoprotein receptor, wherein the target glycoprotein receptor is a cell surface glycoprotein such as a cell surface receptor, the sample comprising the cells is first subjected to a lysis step and subsequently the cellular proteins are digested using enzymes such as trypsin to obtain a processed cell sample comprising the dual peptide-bound complex.

In case of a method of identifying specific interactions between a ligand and a target glycoprotein receptor, wherein the target glycoprotein receptor is a secreted glycoprotein, the sample comprising the secreted glycoprotein in a biological fluid is digested using enzymes such as trypsin to obtain a processed cell sample comprising the dual peptide-bound complex.

The dual peptide-bound complex is then affinity purified using its third functionality which is the affinity group. If e.g. biotin is used as the affinity group, the dual peptide-bound complex is affinity purified using streptavidin beads according to standard procedures (Wollscheid et al. ibid).

Thus step (iv) of the above method preferably includes isolating and purifying the dual peptide-bound complex from the sample by first subjecting the sample to enzymatic digestion to obtain a processed sample followed by affinity purification of the captured peptides out of the processed sample.

In a fifth step, N-glycopeptides are specifically released from the beads by protease or glycanase treatment e.g., by exposure to an agent such as PNGase F, PNGase A, etc., preferably using PNGaseF. PNGaseF treatment cleaves between the innermost component of the oligosaccharide structure and the asparagine of the glycopeptide in the N-X-S/T glycosylation motive of the peptide (wherein N stands for asparagine, X stands for any amino acid except proline, and S/T for serine or threonine, respectively), thereby effecting peptide release (and concomitantly deamidation of the asparagine).

Although exemplified herein with N-linked glycosylation sites, it is understood that methods of the invention can also be used with other types of authentically identified glycosylation sites, such as O-linked glycosylation sites or possibly with other types of posttranslational modifications (e.g. attachment of glycosylphosphatidylinositol to the C-terminus of peptides) or glycosylated organic compounds other than proteins such as glycolipids etc.

Thus step (v) of the above method preferably includes separating the captured peptides from the purified dual peptide-bound complex obtained in step (iv) by subjecting it to glycosidase treatment, preferably treatment with different endo- and exoglycosidases, to obtain released peptides. Alternatively, cleavable linkers may be used, e.g. disulfide bond or cis diol containing linkers that can be cleaved with reducing agents or periodate, respectively.

In a sixth step, the so obtained released peptides are analyzed preferably by mass spectrometry. Methods of mass spectrometry analysis are well known to those skilled in the art (see, for example, Yates, J. Mass Spect. 33:1-19 (1998); Kinter and Sherman, Protein Sequencing and Identification Using Tandem Mass Spectrometry, John Wiley and Sons, New York (2000); Aebersold and Goodlett, Chem. Rev. 101:269-295 (2001)). For high resolution polypeptide fragment separation, liquid chromatography ESI-MS/MS or automated LC-MS/MS, which utilizes capillary reverse phase chromatography as the separation method, can be used (Yates et al., Methods Mol. Biol. 112:553-569 (1999)). Preferably, data dependent collision-induced dissociation (CID) with dynamic exclusion will be used as the mass spectrometric method of choice (Goodlett et al., Anal. Chem. 72:1112-1118 (2000)). For such an analysis, mass spectrometers are typically operated in the data dependent mode in which ion signals above a predetermined threshold automatically trigger the instrument to switch from MS to MS/MS mode for generating collision-induced dissociation (CID) spectra of peptides.

All MS/MS spectra are searched against a standard protein database using standard algorithms (SEQUEST, Mascot, X!tandem, OMSSA, . . . ) and are typically filtered in order to limit the false-positive protein identification rate to below 1%. Additionally, all peptides are filtered for the N115-X-S/T motif of formerly glycosylated peptides.

Thus step (vi) of the above method preferably includes analyzing the released peptides obtained in step (v) by quantitative mass spectrometric methods to identify the interaction between the ligand and the target glycoprotein receptor.

The concentration of glycoproteins in the ligand sample can quantitatively be compared to the control sample in order to detect specific enrichments of target glycoprotein receptors. For this label-free mass spectrometric quantification, the reversed phase chromatography immediately preceding the mass spectrometric analysis can be displayed as a MS feature map in which the retention time of features is plotted against their mass/charge ratio. As detected by the mass spectrometer, peptides in such a map appear in distinct isotopic patterns over a defined time and with a defined ion current intensity according to their abundance in the sample. Once the peptides have been identified through fragmentation and MS/MS analysis, this information can be assigned to specific peptide features in the MS map and combined with the semi-quantitative data with open source or commercial algorithms like Superhim (Mueller et al. Proteomics (2007) vol. 7 (19) pp. 3470-3480), or Progenesis LC-MS (Nonlinear Dynamics). MS feature maps of different samples (e.g. sample vs control) can then be overlaid and compared in order to get ratios for the peptide abundances. For stochastically tagged peptides from glycoproteins these ratios should be around 1 and glycoprotein receptor peptides that are specifically captured in a ligand-based fashion get higher values in the ligand sample vs. control. If proteins are identified with more than one peptide, the abundance information can be combined.

In other embodiments, alternative mass spectrometry-based quantification methods can be used such as single reaction monitoring (SRM) and stable isotope labeling with amino acids in cell culture (SILAC) (Nilsson et al. Mass spectrometry in high-throughput proteomics: ready for the big time. Nat Methods (2010) vol. 7 (9) pp. 681-5)

In yet a further aspect the invention is also directed towards a kit comprising a trifunctional crosslinking reagent according to the invention carrying on three different branches a (protected) hydrazine group, a ligand-reactive group, an affinity group, such as a trifunctional crosslinking reagent as defined herein.

The present invention is further illustrated by the following non-limiting examples:

EXAMPLES

Materials and Methods

Reactions were performed in flame-dried glassware under an atmosphere of dry argon. All chemicals were purchased from Fluka, Acros, Aldrich, Merk and Lancaster and used without further purification. Dry triethylamine (TEA) was distilled over $CaH_2$ and diisopropylethylamine (DIPEA) was distilled from KOH and methanol (MeOH) was distilled over magnesium oxide. N,N'-Dimethylformamide (DMF) was dried over molecular sieves. $CH_2Cl_2$ was dried by passage over activated alumina under an argon atmosphere ($H_2O$ content <30 ppm, Karl Fischer titration). Reactions were magnetically stirred and monitored by thin layer chromatography (TLC) using Merck Silica Gel 60 $F_{254}$ plates and visualized by fluorescence quenching under UV light. In addition, TLC plates were stained using nynhydrin (in n-butanol and 10% sulfuric acid) and potassium permanganate. Chromatographic purification of products was performed on E. Merck Silica Gel 60 (230-400 mesh) or Sephadex LH-20 (Aldrich). Concentration under reduced pressure was performed by rotary evaporation at 40° C. (unless otherwise specified) at the appropriate pressure. NMR spectra were recorded on a Varian Mercury 300 spectrometer, Bruker DRX 400 and Bruker DRX 600 spectrometer. Chemical shifts are reported in ppm with the solvent resonance as the internal standard. Data are reported as follows: s=singlet, brs=broad singlet, d=doublet, t=triplet, q=quartet, m=multiplet; coupling constants in Hz. IR spectra were recorded on a PerkinElmer Spectrum RXI FT-IR spectrophotometer. Absorptions are given in wave numbers ($cm^{-1}$). Exact mass spectra were obtained with Ion Spec an Ultima 4.7 spectrometer MALDI-FT by the LOC MS service of ETH Zurich. Peaks are given in percent (m/z). Abbreviation: Boc, butoxycarbonyl; DMAP, 4-dimethylaminopyridine; EDCI, 1-(3-dimethylaminopropyl)-3-ethylcarbodiimide hydrochloride; $Et_2O$, diethylether; EtOH, ethanol; Fmoc, 9-fluorenylmethoxycarbonyl; HBTU, N,N,N',N'-tetramethyl-O-(1H-benzotriazol-1-yl)uronium hexafluorophosphate; NHS, N-hydroxysuccinimide; TFA, trifluoroacetic acid; TFAA, trifluoroacetic anhydride; DMSO, dimethylsulfoxide; i-PrOH, isopropanol; DCC, N,N'-dicycloheylcarbodiimide; Hex, hexane.

Quantification assay: For the analysis, mass spectrometers are operated in the data dependent mode in which ion signals above a predetermined threshold automatically trigger the instrument to switch from MS to MS/MS mode for generating collision-induced dissociation (CID) spectra of peptides. All MS/MS spectra are searched against a standard protein database and the identified peptides are filtered for the presence of the N115-X-S/T motif. The concentration of (cell surface or secreted) peptides in the ligand sample is quantitatively compared to the control sample in order to detect specific enrichments of target receptors. For stochastically tagged peptides from (cell surface or secreted) proteins, ratios should be around 1 and glycoprotein receptor peptides that are specifically captured in a ligand-based fashion get higher values in the ligand sample vs. control. If proteins are identified with more than one peptide, the abundance information can be combined. Further details can be found in the specific Examples.

Example 1

Synthesis of Crosslinker Joy-06-16

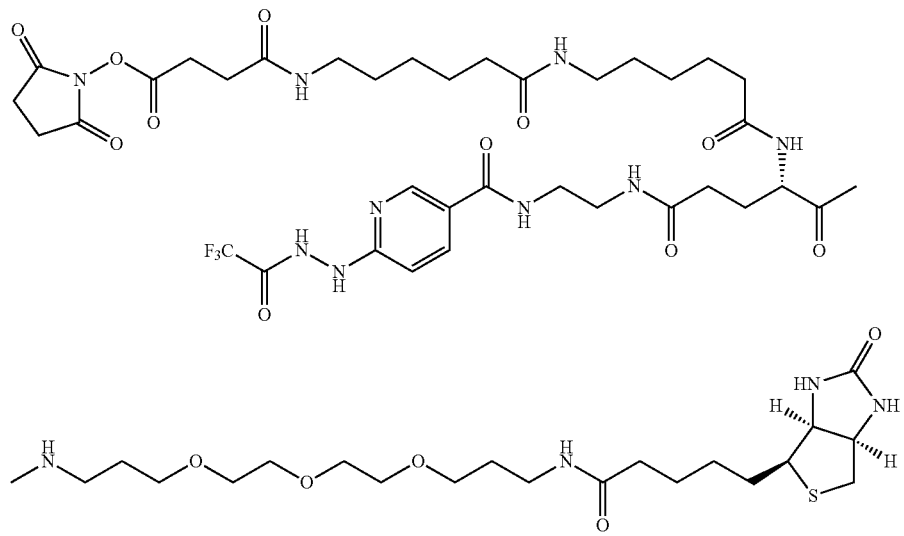

(a) Synthesis of (2S)-2-[6-(6-{[(tert-Butoxy)carbonyl]amino}hexanamido)hexanamido]-5-methoxy-5-oxopentanoic Acid (1)

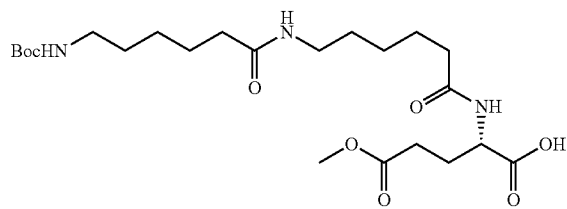

To a solution of (2S)-2-Amino-5-methoxy-5-oxopentanoic acid (9.8 g, 22 mmol; synthesized according to Glenn, M. P. et al, *J. Am. Chem. Soc.* 2003, 125, 640) in MeOH (130 mL) was added 2,5-Dioxopyrrolidin-1-yl 6-(6-{[(tert-butoxy)carbonyl]amino}hexanamido)hexanoate (5.7 g, 29 mmol; synthesized according to Srinivasan, B. and Huang, X. *Chirality* 2008, 20, 265) and then to the solution was added TEA (9.4 mL, 67 mmol). After stirring for 30 min at room temperature, the reaction mixture was concentrated under reduced pressure and dissolved in EtOAc (200 mL) and then washed with 1N HCl (100 mL) and washed with brine and dried over MgSO$_4$ and concentrated under reduced pressure and purified by flash chromatography (CH$_2$Cl$_2$:MeOH=10:1 to CHCl$_3$:MeOH:H$_2$O=85:15:1 to CHCl$_3$:MeOH:H$_2$O=65:25:4) providing the desired compound as a white foamy solid (9.5 g, 87%).

TLC(CHCl$_3$:MeOH:H$_2$O, 85:15:1 v/v): R$_F$=0.8; m.p. 49-51° C.; $^1$H-NMR (400 MHz, CD$_3$OD): δ 4.36 (dd, J=8.6, 5.1 Hz, 1H), 3.68 (s, 3H), 3.17 (t, J=7.0 Hz, 2H), 3.03 (t, J=7.0 Hz, 2H), 2.43 (t, J=7.2 Hz, 2H), 2.26 (t, J=7.4 Hz, 2H), 2.12-2.15 (m, 2H), 2.00-1.90 (m, 1H), 1.69-1.28 (m, 22H).

(b) Synthesis of 5-[(3aS,4S,6aR)-2-oxo-hexahydro-1H-thieno[3,4-d]imidazolidin-4-yl]-N-(3-{2-[2-(3-aminopropoxy)ethoxy]ethoxy}propyl)pentanamide (2)

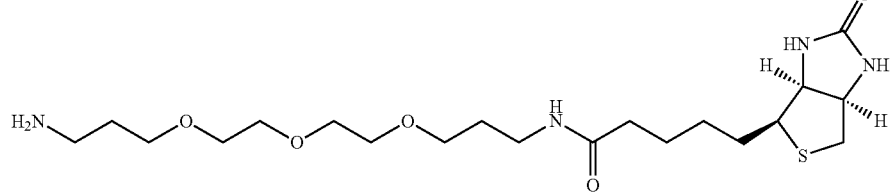

Biotin (6.3 g, 18 mmol) was dissolved in DMF (150 mL) and then to the solution was added DIPEA (3.2 mL, 18 mmol) and HBTU (7.0 g, 18 mmol) then was stirred at mom temperature for 10 min. To the reaction mixture was added N-Boc-4,7,10-trioxatridecane-1,13-diamine (5.9 g, 18 mmol) and then stirred at room temperature for 1 hr. The mixture was concentrated under reduced pressure, the residue was taken up in CH$_2$Cl$_2$ (500 mL) and washed (1N HCl×2, saturated NaHCO$_3$), dried over MgSO$_4$ and filtered. The filtrate was concentrated under reduced pressure to provide N-Boc-N'-biotinyl-4,7,10-trioxatridecane-1,13-diamine as a brown oil. N—Boc-N'-Biotinyl-4,7,10-trioxatridecane-1,13-diamine was stirred in TFA (200 mL) with water (1 drop). After 1 hr, then evaporated under reduced pressure and purified by flash chromatography (CH$_2$Cl$_2$:MeOH=10:1 to CHCl$_3$:MeOH:H$_2$O=10:6:1 with TEA) providing the desired compound as a slightly brown oil (7.4 g, 90%).

TLC (CHCl$_3$:MeOH, 3:1 v/v): R$_F$=0.2; $^1$H-NMR (400 MHz, CD$_3$OD): δ 4.57 (dd, J=7.7, 4.7 Hz, 1H), 4.38 (dd, J=7.8, 4.5 Hz, 1H), 3.80-3.65 (m, 12H), 3.58 (t, J=6.1 Hz, 2H), 3.33-3.25 (m, 5H), 3.16 (t, J=6.4 Hz, 2H), 3.00 (dd, J=12.8, 5.0 Hz, 1H), 2.77 (d, J=12.7 Hz, 1H), 2.27 (t, J=7.4 Hz, 2H), 2.05-1.95 (m, 2H), 1.85-1.61 (m, 4H), 1.54-1.46 (m, 2H); $^{13}$C-NMR (101 MHz, CD$_3$OD): δ 176.0, 166.1, 71.4, 71.2, 71.1, 70.3, 69.8, 63.4, 61.7, 57.0, 41.1, 40.0, 37.7, 36.9, 30.5, 29.8, 29.6, 28.1, 26.9; HRMS (m/z): [M+H]$^+$ calcd for C$_{20}$H$_{38}$N$_4$O$_5$S, 446.26; found 447.2; IR (neat): 3289, 2928, 2873, 1673, 1551, 1463, 1431, 1200, 1177, 1126 cm$^{-1}$.

(c) Synthesis of Methyl (4S)-4-[(3-{2-[2-({9-[(3aS, 4S,6aR)-2-oxo-hexahydro-1H-thieno[3,4-d]imidazolidin-4-yl]-5-oxononyl}oxy)ethoxy]ethoxy}propyl)carbamoyl]-4-[6-(6-{[(tert-butoxy)carbonyl]amino}hexanamido)hexanamido]butanoate (3)

min, compound 2 (6.6 g, 15 mmol) was added, and the mixture was stirred for 1 hr. The crude mixture was concentrated under reduced pressure and purified by column chromatography (CH$_2$Cl$_2$:MeOH=10:1 to CHCl$_3$:MeOH:H$_2$O=10:6:1) to provide the desired compound as a white viscous foam (7.5 g, 55%).

TLC (CHCl$_3$:MeOH:H$_2$O, 65:25:4 v/v): R$_F$=0.8; $^1$H-NMR (400 MHz, CD$_3$OD): δ 4.57 (ddd, J=7.9, 5.0, 0.9 Hz, 1H), 4.39 (dt, J=8.0, 4.8 Hz, 2H), 3.75 (s, 3H), 3.73-3.58 (m, 12H), 3.39-3.22 (m, 7H), 3.10 (t, J=7.0 Hz, 2H), 3.01 (dd, J=12.7, 5.0 Hz, 1H), 2.79 (d, J=12.7 Hz, 1H), 2.47 (t, J=7.6 Hz, 2H), 2.35-2.23 (m, 6H), 2.21-2.11 (m, 1H), 2.03-1.93 (m, 1H), 1.87-1.36 (m, 31H).

(d) Synthesis of (4S)-4-[(3-{2-[2-({9-[(3aS,4S, 6aR)-2-Oxo-hexahydro-1H-thieno[3,4-d]imidazolidin-4-yl]-5-oxononyl}oxy)ethoxy]ethoxy}propyl)carbamoyl]-4-[6-(6-{[(tert-butoxy)carbonyl]amino}hexanamido)hexanamido]butanoic Acid (4)

4

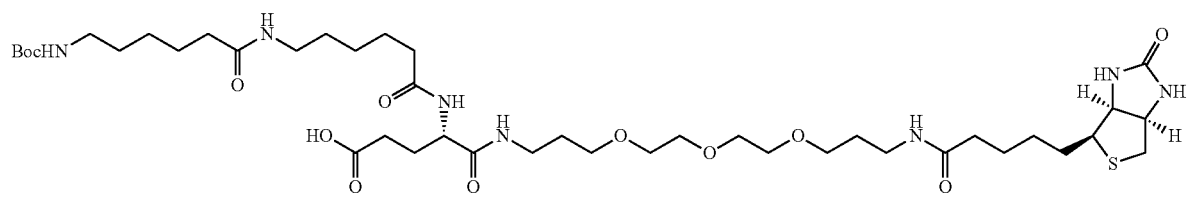

The ester compound 3 (0.62 g, 0.68 mmol) was dissolved in CaCl$_2$ (0.8 M) in i-PrOH:H$_2$O (7:3) (13.4 mL) and then was added of 0.5 M NaOH (1.6 mL) at room temperature After 2 hr, the reaction mixture was neutralized with 5 M HCl and then it was extracted with CHCl$_3$ with 3 times (100 mL) then was dried over Na$_2$SO$_4$ then concentrated under reduced pressure and purified by flash chromatography (CHCl$_3$:MeOH:H$_2$O=85:15:1 to 65:25:4) providing the desired compound as a colorless viscous foam (0.24 g, 39%).

TLC (CHCl$_3$:MeOH:H$_2$O, 10:6:1 v/v): R$_F$=0.4; $^1$H-NMR (300 MHz, CD$_3$OD): δ 8.00 (t, J=4.9 Hz, 1H), 7.93 (m, 1H), 4.51 (ddd, J=5.0, 0.8, 7.9 Hz, 1H), 4.35-4.31 (m, 2H), 3.67-3.53 (m, 12H), 3.31-3.21 (m, 5H), 3.18 (t, J=7.0 Hz, 2H), 3.04 (t, J=7.0 Hz, 2H), 2.95 (dd, J=12.7, 5.0 Hz, 1H),

3

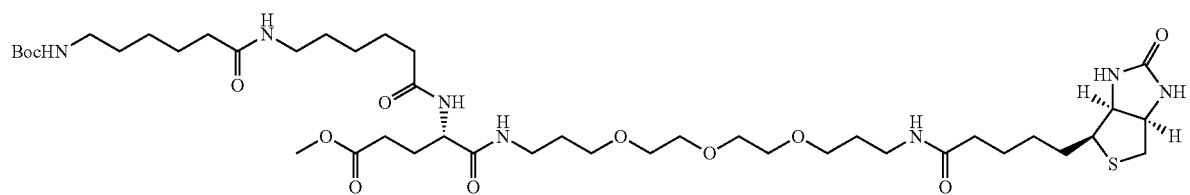

Compound 1 (9.4 g, 19 mmol), HBTU (7.3 g, 19 mmol), and DIPEA (3.4 mL, 19 mmol) were dissolved in anhydrous DMF (90 mL), and stirred at room temperature. After 10

2.73 (d, J=12.7 Hz, 1H), 2.38 (t, J=7.6 Hz, 2H), 2.28 (t, J=7.5 Hz, 2H), 2.23-2.18 (m, 4H), 2.11-2.05 (m, 1H), 1.95-1.89 (m, 1H), 1.80-1.32 (m, 31H).

(e) Synthesis of tert-Butyl N-{5-[(5-{[(1S)-1-[(3-{2-[2-(3-{5-[(3aS,4S,6aR)-2-oxo-hexahydro-1H-thieno[3,4-d]imidazolidin-4-yl]pentanamido}propoxy)ethoxy]ethoxy}propyl)carbamoyl]-3-[(2-{[(9H-fluoren-9-ylmethoxy)carbonyl]amino}ethyl)carbamoyl]propyl]carbamoyl}pentyl)carbamoyl]pentyl}carbamate (5)

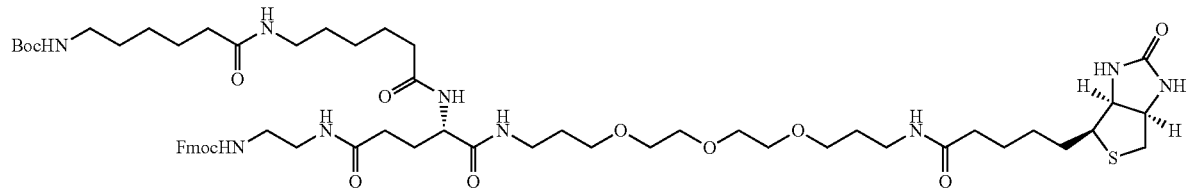

To a solution of 4 (3.4 g, 3.8 mmol) in DMF (50 mL) was added HBTU (1.7 g, 4.6 mmol) and DIPEA (0.80 mL, 4.6 mmol). After stirring for 10 min at room temperature, to the reaction mixture was added N-1-Fmoc-1,2-diaminoethane hydrochloride (1.3 g, 4.6 mmol) and then stirred for 30 min. The solvent was evaporated under reduced pressure and purified by flash chromatography ($CH_2Cl_2$:MeOH=10:1 to $CHCl_3$:MeOH:$H_2O$=65:25:4) providing the desired compound as a colorless viscous foam (4.3 g, 97%).

TLC ($CHCl_3$:MeOH:$H_2O$, 65:25:4 v/v): $R_F$=0.8; $^1$H-NMR (400 MHz, $CD_3OD$): δ 7.82 (d, J=7.6 Hz, 2H), 7.67 (d, J=7.5 Hz, 2H), 7.41 (t, J=7.6 Hz, 2H), 7.33 (t, J=7.6 Hz, 2H), 4.49 (dd, J=7.5, 4.8 Hz, 1H), 4.35-4.30 (m, 3H), 4.22 (t, J=6.8 Hz, 1H), 3.66-3.48 (m, 12H), 3.28-3.14 (m, 10H), 3.05 (dd, J=6.9, 4.2 Hz, 2H), 2.93 (dd, J=12.7, 5.0 Hz, 1H), 2.72 (d, J=12.7 Hz, 1H), 2.29-2.16 (m, 8H), 2.12-2.05 (m, 1H), 1.94-1.89 (m, 1H), 1.78-1.61 (m, 12H), 1.48-1.29 (m, 21H).

(f) Synthesis of tert-Butyl N-{5-[(5-{[(1S)-1-[(3-{2-[2-({9-[(3aS,4S,6aR)-2-oxo-hexahydro-1H-thieno[3,4-d]imidazolidin-4-yl]-5-oxononyl}oxy)ethoxy]ethoxy}propyl)carbamoyl]-3-[(2-{[6-(2,2,2-trifluoroacetohydrazido)pyridin-3yl]formamido}ethyl)carbamoyl]propyl]carbamoyl}pentyl)carbamoyl]pentyl}carbamate (6)

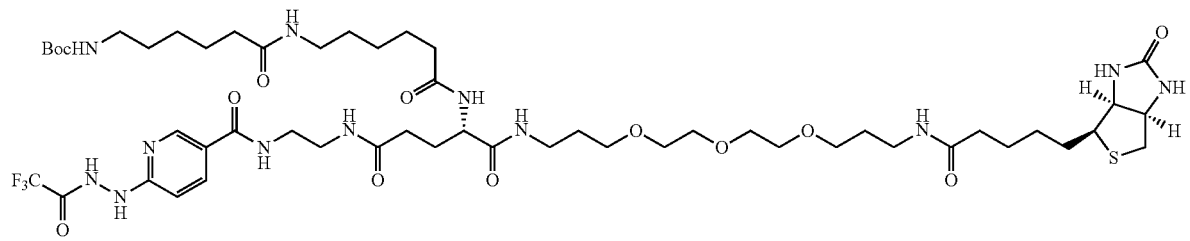 [SMILES: CC(C)(C)OC(=O)NCCCCCC(=O)NCCCCCC(=O)N[C@@H](CCC(=O)NCCNC(=O)c1ccc(NNC(=O)C(F)(F)F)nc1)C(=O)NCCCOCCOCCOCCCNC(=O)CCCC[C@@H]1SC[C@@H]2NC(=O)N[C@@H]21]

To a solution of 5 (4.4 g, 3.8 mmol) in DMF (40 mL) was added piperidine (20% of solvent, 8 mL) and the reaction mixture was stirred for 20 min at room temperature and added to $Et_2O$ (500 mL). Diethyl ether was decanted and the crude compound was poured diethyl ether (250 mL) two times and then the syrup compound was dissolved in MeOH (100 mL) and concentrated under reduced pressure and 2.4 g of the product was carried forward without further purification. The product (2.4 g, 2.6 mmol) and 6-(2,2,2-trifluoroacetohydrazido)pyridine-3-carboxylic acid (1.3 g, 5.2 mmol; synthesized according to Abrams, M. J. et al, *J. Nucl. Med.* 1990, 31, 2022) were dissolved in DMF (30 mL) and EDCI (1.1 g, 5.2 mmol) and DMAP (63 mg, 0.52 mmol) were added to the reaction mixture and stirred for 3 hr at room temperature. The solvent was evaporated under reduced pressure and purified by flash chromatography ($CH_2Cl_2$:MeOH=10:1 to $CHCl_3$:MeOH:$H_2O$=65:25:4) providing the desired compound as a yellow viscous foam (1.6 g, 53%).

TLC ($CHCl_3$:MeOH:$H_2O$, 10:6:1 v/v): $R_F$=0.7; $^1$H-NMR (500 MHz, $CD_3OD$): 10.10 (dd, J=2.3, 0.6 Hz, 1H), 10.05 (t, J=5.6 Hz, 1H), 9.98 (t, J=6.1 Hz, 1H), 9.76 (t, J=5.6 Hz, 1H), 9.70 (dd, J=13.5, 6.8 Hz, 1H), 9.64 (dd, J=7.7, 3.5 Hz, 1H), 9.59-9.55 (m, 2H), 9.50-9.46 (m, 2H), 8.34 (d, J=8.8, 1H), 8.13-8.09 (m, 2H), 7.99 (s, 1H), 6.04 (dd, J=7.8, 5.0 Hz, 1H), 5.86-5.77 (m, 2H), 5.19-4.96 (m, 16H), 4.80-4.68 (m, 7H), 4.57 (dd, J=13.0, 7.0 Hz, 2H), 4.48 (dd, J=12.7, 5.0 Hz, 1H), 4.25 (d, J=12.6 Hz, 1H), 3.83-3.78 (m, 4H), 3.75-3.69 (m, 4H), 3.64-3.56 (m, 1H), 3.48-3.38 (m, 1H), 3.32-2.84 (m, 31H).

(g) Synthesis of 3-({5-[(5-{[(1S)-1-[(3-{2-[2-(3-{5-[(3aS,4S,6aR)-2-Oxo-hexahydro-1H-thieno[3,4-d]imidazolidin-4-yl]pentanamido}propoxy)ethoxy]ethoxy}propyl)carbamoyl]-3-[(2-{[6-(2,2,2-trifluoroacetohydrazido)pyridin-3yl]formamido}ethyl)carbamoyl]propyl]carbamoyl}pentyl)carbamoyl]pentyl}carbamoyl)propanoic Acid (7)

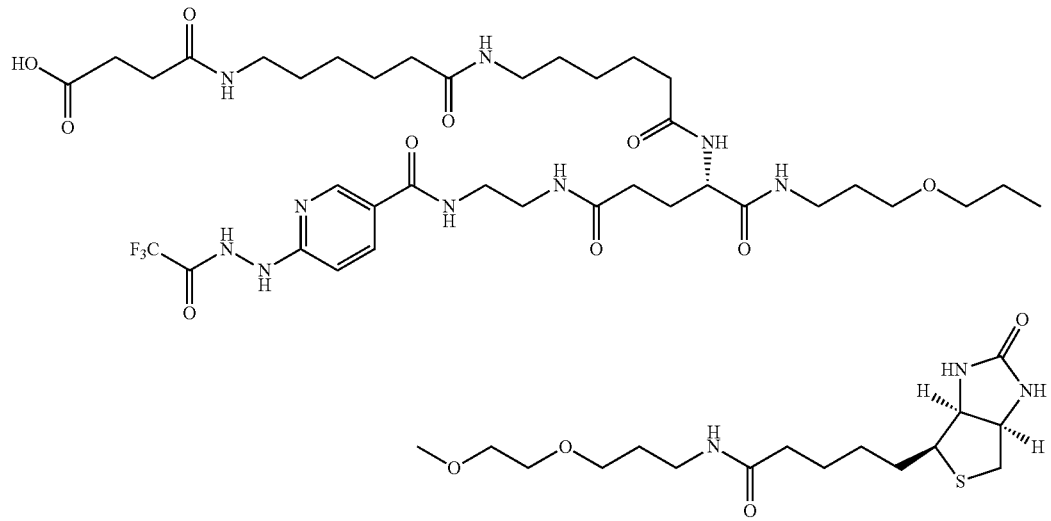

Compound 6 (20 mg, 18 μmol) was dissolved in TFA (0.5 mL) and evaporated and dried in vacuum. Without further purification, the product (18 mg, 18 μmol) was dissolved in DMF (1 mL) then was added DIPEA (4.3 μl, 19 μmol) and succinic anhydride (2.2 mg, 19 μmol) and stirred at room temperature after 3 hr then the crude mixture was evaporated under reduced pressure and purified by flash chromatography ($CH_2Cl_2$:MeOH=10:1 to $CHCl_3$:MeOH:$H_2O$=10:6:1) providing the desired acid compound as a yellow viscous foam in quantitative yield (20 mg).

TLC ($CHCl_3$:MeOH:$H_2O$, 10:6:1 v/v): $R_F$=0.5; $^1$H-NMR (600 MHz, DMF-$d_7$): δ 11.96 (brs, 1H), 9.30 (brs, 1H), 8.67 (d, J=1.8 Hz, 1H), 8.42 (t, J=5.4 Hz, 1H), 8.11-8.07 (m, 2H), 7.97 (dd, J=8.0, 3.6 Hz, 1H), 7.92 (td, J=5.6, 2.8 Hz, 1H), 7.82 (t, J=5.4 Hz, 1H), 7.75 (dd, J=12.9, 5.5 Hz, 2H), 6.86 (d, J=8.7 Hz, 1H), 6.45 (brs, 1H), 6.36 (s, 1H), 4.49-4.47 (m, 1H), 4.35 (td, J=8.5, 5.2 Hz, 1H), 4.30 (ddd, J=6.7, 4.4, 1.9 Hz, 1H), 3.82-3.75 (m, 1H), 3.37 (m, 17H), 3.33-3.329 (m, 2H), 3.25-3.19 (m, 5H), 3.13 (dd, J=12.9, 6.9 Hz, 4H), 2.94 (d, J=7.4 Hz, 1H), 2.72 (d, J=12.4 Hz, 1H), 2.56 (t, J=7.1 Hz, 2H), 2.45 (t, J=7.0 Hz, 2H), 2.27-2.22 (dt, J=10.5, 5.0 Hz, 4H), 2.18-2.13 (m, 4H), 2.10-2.06 (m, 1H), 1.89-1.83 (m, 1H), 1.79-1.68 (m, 5H), 1.64-1.54 (m, 7H), 1.48-1.28 (m, 12H).

(h) Synthesis of 2,5-Dioxopyrrolidin-1-yl 3-({5-[(5-{[(1S)-1-[(3-{2-[2-({9-[(3aS,4S,6aR)-2-oxo-hexahydro-1H-thieno[3,4-d]imidazolidin-4-yl]-5-oxononyl}oxy)ethoxy]ethoxy}propyl)carbamoyl]-3-[(2-{[6-(2,2,2-trifluoroacetohydrazido)pyridin-3-yl]formamido}ethyl)carbamoyl]propyl]carbamoyl}pentyl)carbamoyl]pentyl}carbamoyl)propanoate (8)

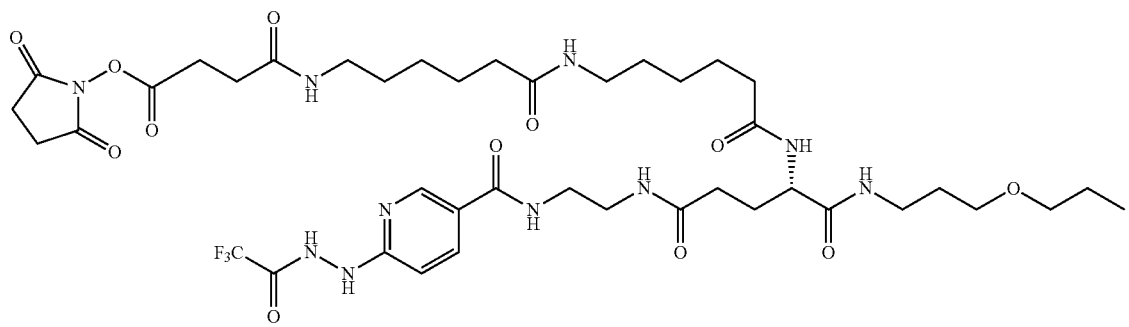

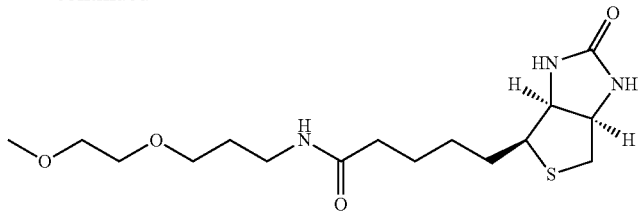

The product 7 (84 mg, 71 μmol), EDCI (34 mg, 18 μmol) and NHS (19 mg, 16 μmol) were dissolved in DMF (1 mL) and then to the reaction mixture was stirred at room temperature overnight. The result mixture was evaporated under reduced pressure and purified by flash chromatography (CHCl$_3$:MeOH:H$_2$O=10:6:1) providing the desired compound as a yellow viscous foam (51 mg, 56%).

TLC (CHCl$_3$:MeOH:H$_2$O, 10:6:1 v/v): R$_F$=0.7; $^1$H-NMR (400 MHz, CD$_3$OD): δ 8.63 (d, J=1.9 Hz, 1H), 8.10 (dd, J=8.8, 2.3 Hz, 1H), 6.83 (d, J=8.9 Hz, 1H), 4.55 (dd, J=7.6, 4.7 Hz, 1H), 4.38-4.34 (m, 2H), 3.75-3.48 (m, 16H), 3.35-3.20 (m, 12H), 3.01-32.97 (m, 2H), 2.89 (s, 3H), 2.74 (s, 3H), 2.64 (t, J=7.0 Hz, 2H), 2.35-2.21 (m, 6H), 2.17-2.05 (m, 1H), 1.98-1.91 (m, 1H), 1.67 (m, 22H).

Example 2

Synthesis of Crosslinker Joy-05-125

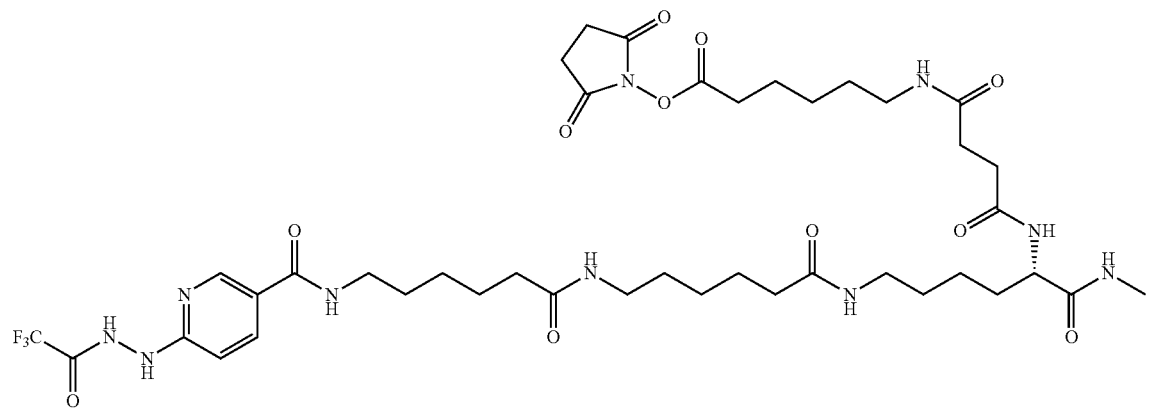

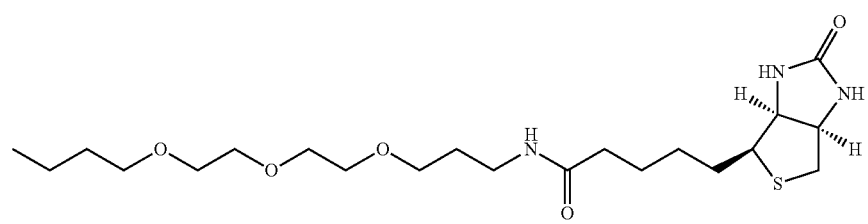

(a) Synthesis of tert-Butyl N-[(5S)-5-[(3-{2-[2-({9-[(3aS,4S,6aR)-2-oxo-hexahydro-1H-thieno[3,4-d]imidazolidin-4-yl]-5-oxononyl}oxy)ethoxy]ethoxy}propyl)carbamoyl]-5-{[(9H-fluoren-9-ylmethoxy)carbonyl]amino}pentyl]carbamate (9)

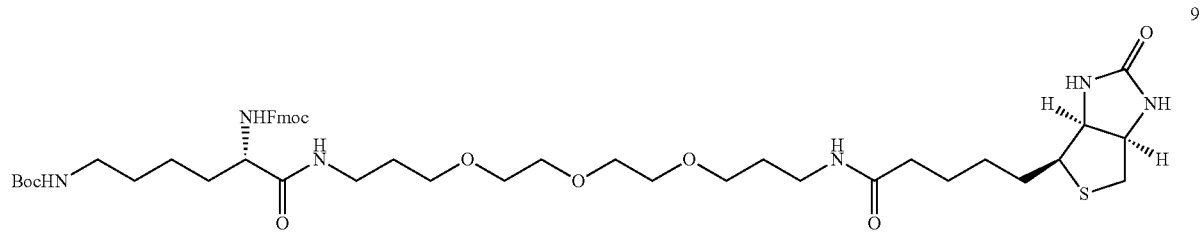

9

Fmoc-N-ε-Boc-L-Lysine (1.7 g, 3.7 mmol) was dissolved in DMF (20 mL) and then to the solution were added DIPEA (0.63 mL, 3.7 mmol) and HBTU (1.7 g, 4.4 mmol) and after 10 min then to the reaction mixture was added a solution of 1-N-biotinyl-4,7,10-trioxatridecane-1,13-diamine (1.8 g, 4.1 mmol) in DMF (5 mL) and stirred at room temperature for 1 hr and then the solvent was evaporated under reduced pressure and purified by flash chromatography (CHCl$_3$:MeOH:H$_2$O=10:6:1) providing the desired compound as a white viscous foam (2.6 g, 78%).

TLC (CH$_2$Cl$_2$:MeOH, 10:1 v/v): R$_F$=0.2; $^1$H-NMR (400 MHz, CD$_3$OD): δ 7.86 (d, J=7.5 Hz, 2H), 7.73 (dd, J=6.5, 4.7 Hz, 2H), 7.48-7.36 (m, 4H), 4.53 (dd, J=7.8, 4.3 Hz, 1H), 4.46 (t, J=6.2 Hz, 2H), 4.33 (dd, J=7.9, 4.5 Hz, 1H), 4.28 (t, J=6.7 Hz, 1H), 4.09 (dd, J=8.3, 5.3 Hz, 1H), 3.66-3.53 (m, 12H), 3.36-3.29 (m, 4H), 3.27-3.20 (m, 1H), 3.10 (t, J=6.8 Hz, 2H), 2.96 (dd, J=12.7, 5.0 Hz, 1H), 2.76 (d, J=12.7 Hz, 1H), 2.24 (t, J=7.4 Hz, 2H), 1.85-1.41 (m, 25H); HRMS (m/z): [M+Na]$^+$ calcd for C$_{46}$H$_{68}$N$_6$O$_{10}$S, 896.47; found 919; IR (neat): 3283, 2929, 2866, 1690, 1652, 1529, 1365, 1247, 1166, 1102, 1042, 843, 741 cm$^{-1}$.

(b) Synthesis of tert-Butyl N-{5-[(5-{[(5S)-5-[(3-{2-[2-({9-[(3aS,4S,6aR)-2-oxo-hexahydro-1H-thieno[3,4-d]imidazolidin-4-yl]-5-oxononyl}oxy)ethoxy]ethoxy}propyl)carbamoyl]-5-{[(9H-fluoren-9-ylmethoxy)carbonyl]amino}pentyl]carbamoyl}pentyl)carbamoyl]pentyl}carbamate (10)

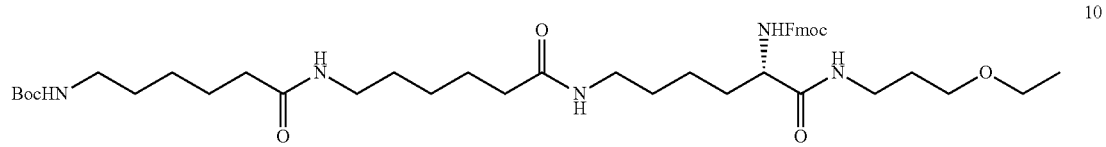

10

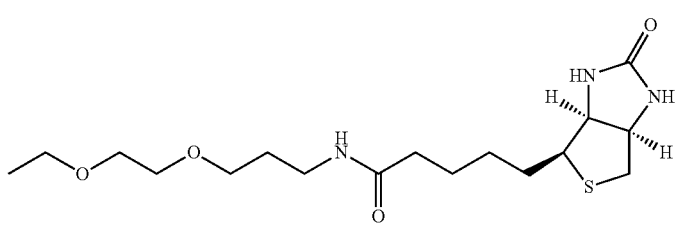

Compound 9 (2.6 g, 2.9 mmol) was stirred in mixture of $CH_2Cl_2$:TFA (1:1, 20 mL) and then stirred at 0° C. for 30 min and then evaporated and dried under high vacuum. The crude product (2.4 g, 3.0 mmol) and 2,5-Dioxopyrrolidin-1-yl 6-(6-{[(tert-butoxy)carbonyl]amino}hexanamido)hexanoate (1.5 g, 3.5 mmol; synthesized according to Srinivasan, B. and Huang, X. *Chirality* 2008, 20, 265) were dissolved in MeOH (6 mL) and then to the mixture was added TEA (0.83 mL, 5.9 mmol) and stirred at room temperature for 20 min and the solvent was evaporated under reduced pressure and purified by flash chromatography ($CH_2Cl_2$:MeOH=9:1 to $CHCl_3$:MeOH:$H_2O$=85:15:1) providing the desired compound as a white viscous foam (2.8 g, 84%).

TLC ($CH_2Cl_2$:MeOH, 10:1 v/v): $R_F$=0.8; $^1$H-NMR (400 MHz, $CD_3OD$): δ 7.85 (d, J=7.5 Hz, 2H), 7.72 (dd, J=6.7, 4.1 Hz, 2H), 7.45 (t, J=7.4 Hz, 2H), 7.37 (td, J=7.5, 1.0 Hz, 2H), 4.52 (dd, J=7.5, 4.6 Hz, 1H), 4.45 (t, J=6.9 Hz, 2H), 4.30 (m, 2H), 4.07 (dd, J=8.3, 5.2 Hz, 1H), 3.63-3.52 (m, 12H), 3.34-3.18 (m, 9H), 3.09-3.05 (m, 2H), 2.95 (dd, J=5.0, 12.7, 1H), 2.77 (d, J=5.7, 1H), 2.26-2.19 (m, 6H), 1.83-1.34 (m, 37H); HRMS (m/z): $[M+Na]^+$ calcd for $C_{58}H_{90}N_8O_{12}S$, 1122.64; found 1146; IR (neat): 3320, 2933, 2864, 2476, 2426, 1705, 1636, 1538, 1426, 1214, 1077, 742 cm$^{-1}$.

(c) Synthesis of tert-Butyl N-{5-[(5-{[(5S)-5-[(3-{2-[2-({9-[(3aS,4S,6aR)-2-oxo-hexahydro-1H-thieno[3,4-d]imidazolidin-4-yl]-5-oxononyl}oxy)ethoxy]ethoxy}propyl)carbamoyl]-5-{[(9H-fluoren-9-ylmethoxy)carbonyl]amino}pentyl]carbamoyl}pentyl)carbamoyl]pentyl}carbamate (11)

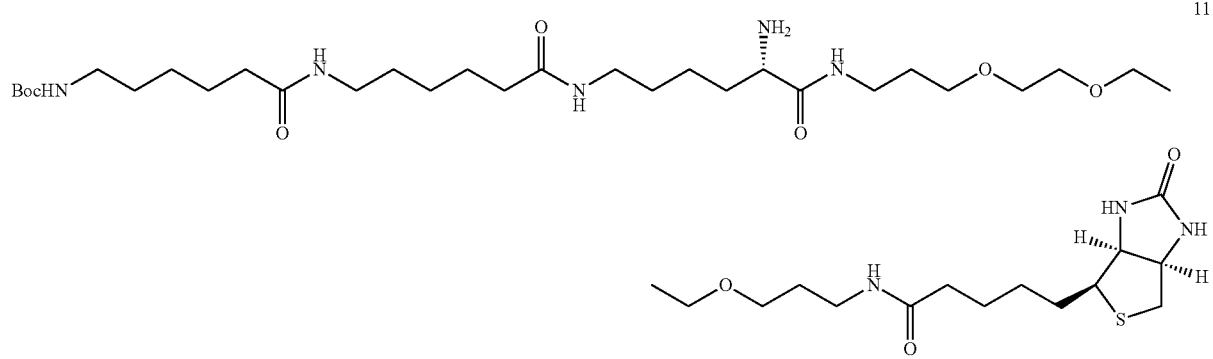

11

Compound 10 (0.39 g, 0.35 mmol) was dissolved in DMF (3 mL) and then to the solution was added piperidine (0.2 mL) at room temperature for 5 min and then to the reaction mixture was added $Et_2O$ (100 mL) and then the ether layer was decanted and then the oil crude mixture was dissolved in MeOH and was concentrated under reduced pressure and purified by flash chromatography ($CHCl_3$:MeOH:$H_2O$=65:25:4 to 10:6:1) providing the desired compound as a white viscous foam (0.21 g, 67%).

TLC ($CH_2Cl_2$:MeOH:$H_2O$, 65:25:4 v/v): $R_F$=0.2; $^1$H-NMR (400 MHz, $CD_3OD$): δ 4.57 (dd, J=7.8, 4.5 Hz, 1H), 4.38 (dd, J=7.9, 4.5 Hz, 1H), 3.72-3.58 (m, 12H), 3.48 (brs, 1H), 3.33-3.21 (m, 9H), 3.10 (t, J=7.0 Hz, 2H), 3.00 (dd, J=12.7, 5.0 Hz, 1H), 2.78 (d, J=12.7 Hz, 1H), 2.29-2.23 (m, 6H), 1.87-1.38 (m, 37H).

(d) Synthesis of 3-{[(1S)-1-[(3-{2-[2-({9-[(3aS,4S,6aR)-2-Oxo-hexahydro-1H-thieno[3,4-d]imidazolidin-4-yl]-5-oxononyl}oxy)ethoxy]ethoxy}propyl)carbamoyl]-5-[6-(6-{[(tert-butoxy)carbonyl]amino}hexanamido)hexanamido]pentyl]carbamoyl}propanoic Acid (12)

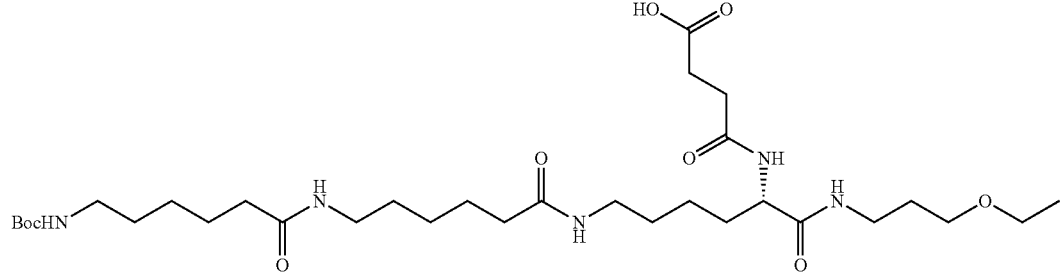

12

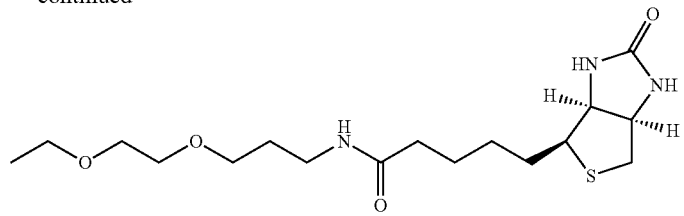

Compound 11 (2.1 g, 2.3 mmol) was dissolved in DMF (1 mL) and then to the solution were added DIPEA (0.48 mL, 2.8 mmol) and succinic anhydride (0.28 g, 2.8 mmol) at room temperature for 1.5 hr and then the solvent was evaporated under reduced pressure and purified by flash chromatography ($CH_2Cl_2$:MeOH=10:1 to $CHCl_3$:MeOH:$H_2O$=65:25:4 to 10:6:1) providing the desired compound as a white viscous foam (1.4 g, 61%).

TLC ($CH_2Cl_2$:MeOH:$H_2O$ with 2 drops of acetic acid, 65:25:4 v/v): $R_F$=0.25; $^1$H-NMR (400 MHz, $CD_3OD$): δ 4.56 (dd, J=7.8, 4.7 Hz, 1H), 4.37 (dd, J=7.9, 4.5 Hz, 1H), 4.31 (dd, J=9.2, 4.9 Hz, 1H), 3.72-3.64 (m, 12H), 3.35-3.20 (m, 9H), 3.09 (t, J=7.0 Hz, 2H), 3.00 (dd, J=12.7, 4.9 Hz, 1H), 2.77 (d, J=12.8 Hz, 1H), 2.69 (dd, J=12.9, 6.0 Hz, 2H), 2.58 (dd, J=13.8, 7.2 Hz, 2H), 2.28-2.22 (m, 6H), 1.94-1.35 (m, 37H).

(e) Synthesis of 6-(3-{[(1S)-1-[(3-{2-[2-({9-[(3aS, 4S,6aR)-2-Oxo-hexahydro-1H-thieno[3,4-d]imidazolidin-4-yl]-5-oxononyl}oxy)ethoxy] ethoxy}propyl)carbamoyl]-5-[6-(6-aminohexanamido)hexanamido]pentyl] carbamoyl}propanamido)hexanoic Acid (13)

Compound 12 (1.3 g, 1.3 mmol), DIPEA (0.27 mL, 1.6 mmol) and HBTU (0.61 g, 1.6 mmol) were dissolved in DMF (15 mL) and after 5 min and then to the solution was added 6-aminocaproic acid (0.21 g, 1.6 mmol) at room temperature and stirred for 1.5 hr and then evaporated under reduced pressure and purified by flash chromatography ($CHCl_3$:MeOH:$H_2O$=85:15:1 to 65:25:4) providing the desired compound as a white viscous foam (1.5 g, quant.).

TLC ($CH_2Cl_2$:MeOH:$H_2O$ with 2 drops of acetic acid, 65:25:4 v/v): $R_F$=0.25; $^1$H-NMR (400 MHz, $CD_3OD$): δ 4.49 (dd, J=7.7, 4.8 Hz, 1H), 4.30 (dd, J=7.8, 4.4 Hz, 1H), 4.26-4.19 (m, 1H), 3.63-3.45 (m, 12H), 3.31-3.12 (m, 11H), 3.03-2.91 (m, 3H), 2.90 (d, J=4.9 Hz, 1H), 2.70 (d, J=13.5 Hz, 1H), 2.28 (t, J=7.3 Hz, 2H), 2.22-2.11 (m, 6H), 2.19-1.31 (m, 38H); HRMS (m/z): [M+H]$^+$ calcd for $C_{48}H_{87}N_9O_{12}S$, 1013.62; found 1015.

The product (1.5 g, 1.3 mmol) was stirred in mixture of $CH_2Cl_2$:TFA (1:1, 20 mL) and then stirred at 0° C. for 10 min and then evaporated and purified by flash chromatography ($CH_2Cl_2$:MeOH=10:1 to $CHCl_3$/MeOH/$H_2O$=10:6:1) providing the desired compound 13 as a white viscous foam (1.4 g, 61%).

$^1$H-NMR (400 MHz, $CD_3OD$): δ 4.56 (dd, J=7.9, 4.2 Hz, 1H), 4.37 (dd, J=7.9, 4.5 Hz, 1H), 4.29 (dd, J=9.2, 4.8 Hz, 1H), 3.71-3.55 (m, 12H), 3.34-3.21 (m, 11H), 3.02-2.97 (m, 3H), 2.77 (d, J=12.7 Hz, 1H), 2.64-2.51 (m, 4H), 2.36 (t, J=7.4 Hz, 2H), 2.29-2.22 (m, 6H), 1.95-1.38 (m, 34H).

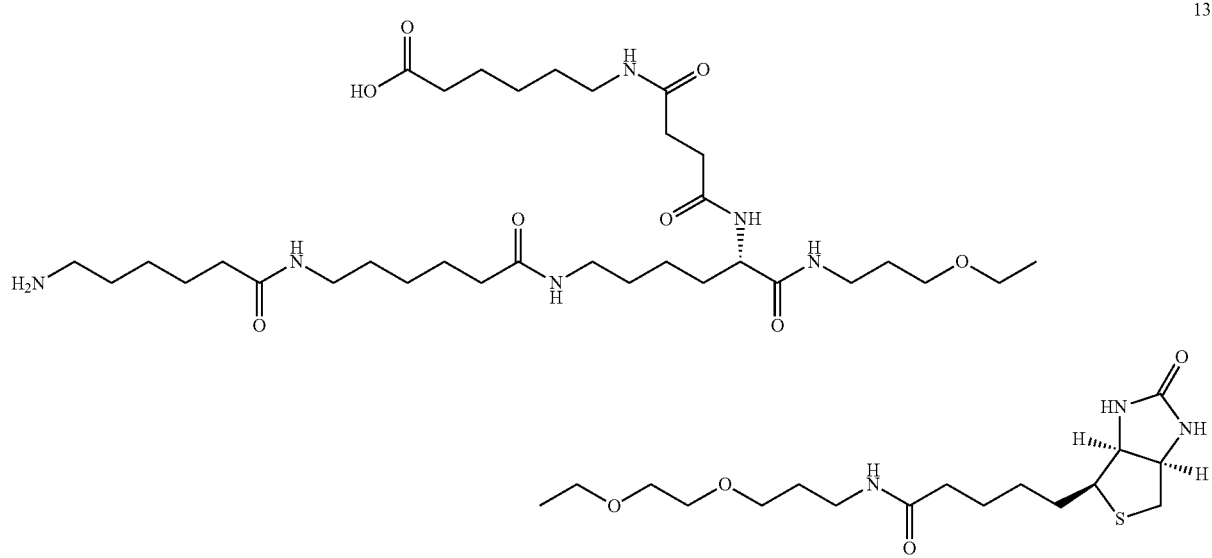

13

(f) Synthesis of 6-(3-{[(1S)-1-[(3-{2-[2-({9-[(3aS,4S,6aR)-2-Oxo-hexahydro-1H-thieno[3,4-d]imidazolidin-4-yl]-5-oxononyl}oxy)ethoxy]ethoxy}propyl)carbamoyl]-5-[6-(6-{[6-({[(tert-butoxy)carbonyl]amino}amino)pyridin-3-yl]formamido}hexanamido)hexanamido]pentyl]carbamoyl}propanamido)hexanoic Acid (14)

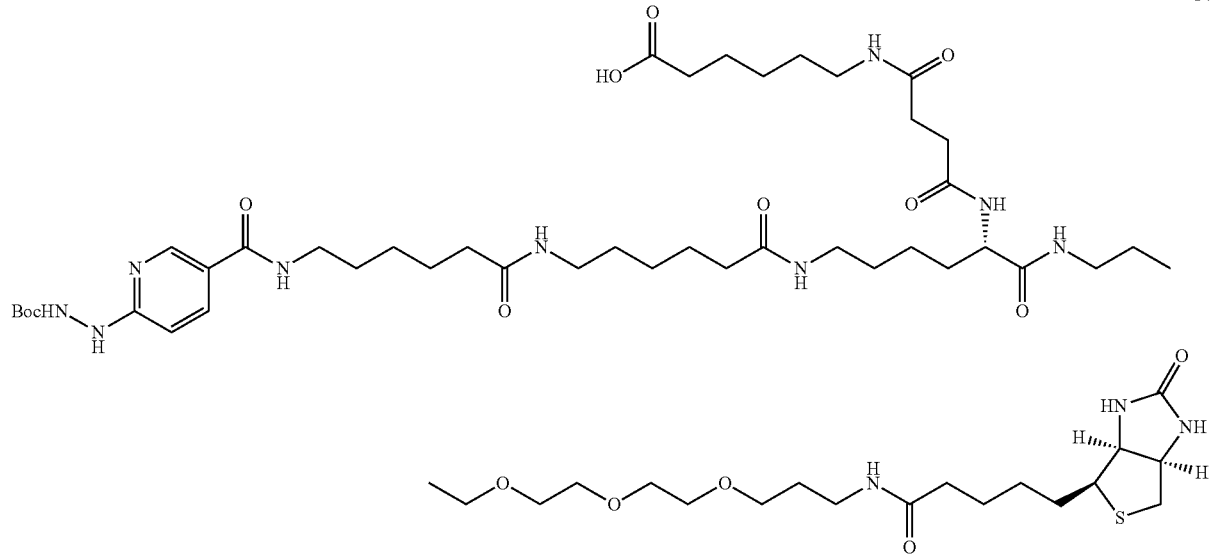

6-({[(tert-Butoxy)carbonyl]amino}amino)pyridine-3-carboxylic acid (0.43 g, 1.7 mmol, synthesized according to Abrams, M. J. et al, *J. Nucl. Med.* 1990, 31, 2022), HBTU (0.51 g, 1.4 mmol) and DIPEA (0.23 mL, 1.4 mmol) were dissolved in DMF (10 mL) at room temperature for 5 min and then to the mixture was added a solution of compound 13 (1.1 g, 1.1 mmol) in DMF (10 mL) and then stirred at room temperature for 40 min then evaporated under reduced pressure and purified by flash chromatography ($CH_2Cl_2$:MeOH=10:1 to $CHCl_3$:MeOH:$H_2O$=65:25:4) providing the desired compound as a slightly yellow viscous foam (0.96 g, 68%).

TLC ($CH_2Cl_2$:MeOH:$H_2O$, 65:25:4 v/v): $R_F$=0.4; $^1$H-NMR (400 MHz, $CD_3OD$): δ 8.60 (d, J=1.7 Hz, 1H), 8.06 (dd, J=8.8, 2.3 Hz, 1H), 6.76 (d, J=8.8 Hz, 1H), 4.55 (dd, J=7.8, 5.0 Hz, 1H), 4.37 (dd, J=7.9, 4.5 Hz, 1H), 4.29 (dd, J=9.2, 4.9 Hz, 1H), 3.71-3.55 (m, 12H), 3.44-3.40 (m, 2H), 3.29-3.19 (m, 11H), 2.99 (dd, J=12.7, 5.0 Hz, 1H), 2.77 (d, J=12.7 Hz, 1H), 2.63-2.50 (m, 4H), 2.35 (t, J=7.4 Hz, 2H), 2.27-2.22 (m, 6H), 1.94-1.35 (m, 43H); HRMS (m/z): [M+Na]$^+$ calcd for $C_{59}H_{100}N_{12}O_{15}S$, 1248.72; found 1271.7; IR (neat): 3249, 3079, 2933, 2863, 1635, 1546, 1459, 1367, 1251, 1160, 1101 cm$^{-1}$.

(f) Synthesis of 6-(3-{[(1S)-1-[(3-{2-[2-({9-[(3aS,4S,6aR)-2-Oxo-hexahydro-1H-thieno[3,4-d]imidazolidin-4-yl]-5-oxononyl}oxy)ethoxy]ethoxy}propyl)carbamoyl]-5-[6-(6-{[6-(2,2,2-trifluoroacetohydrazido)pyridin-3-yl]formamido}hexanamido)hexanamido]pentyl]carbamoyl}propanamido)hexanoic Acid (15)

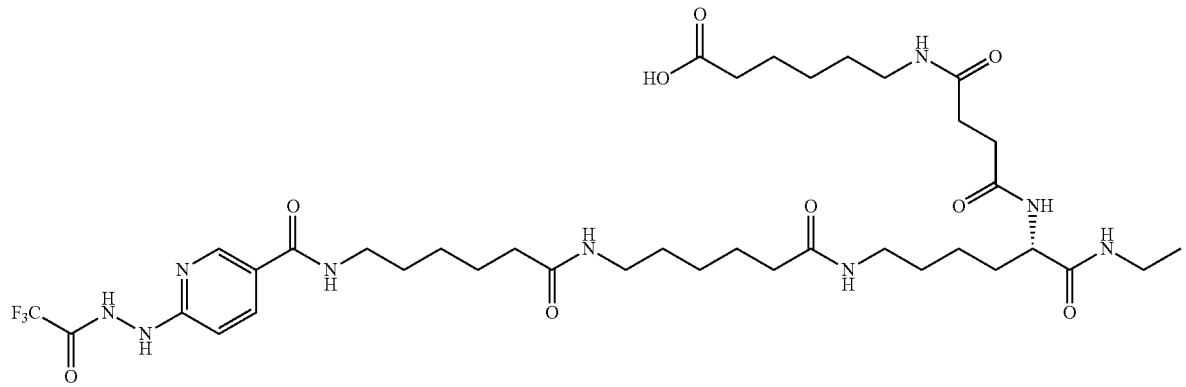

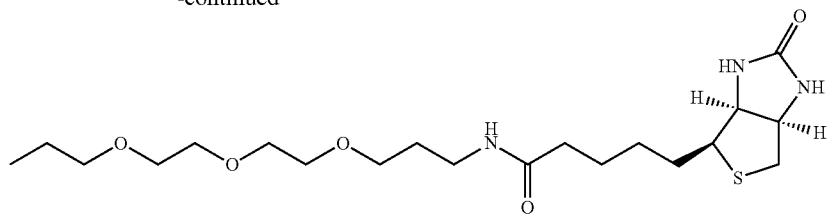

Compound 14 (0.16 g, 0.14 mmol) was dissolved in TFA (4 mL) and then was stirred at room temperature for 30 min and then evaporated and then filtered through the sephadex LH-20 and then dried under vacuum (purple color). The purple amorphous solid was dissolved in DMF (1.5 mL) and then to the solution was added TFAA (21 µL, 0.15 mmol) and then the mixture was stirred at room temperature for 30 min (purple->green yellow). The crude mixture was evaporated under reduced pressure and purified by sephadex LH-20 (CHCl₃/MeOH=95:5) providing the desired compound as a slightly yellow viscous foam (0.14 g, 90%).

TLC (CH$_2$Cl$_2$:MeOH:H$_2$O, 65:25:4 v/v): R$_F$=0.6; $^1$H-NMR (400 MHz, CD$_3$OD): δ 8.60 (d, J=1.9 Hz, 1H), 8.06 (dd, J=8.9, 2.4 Hz, 1H), 7.97 (dd, J=11.5, 5.9 Hz, 2H), 7.19 (d, J=8.8 Hz, 1H), 4.55 (dd, J=7.7, 5.0 Hz, 1H), 4.36 (dd, J=7.8, 4.5 Hz, 1H), 4.29 (dd, J=9.2, 4.8 Hz, 1H), 3.69-3.54 (m, 12H), 3.44-3.40 (m, 2H), 3.33-3.22 (m, 11H), 2.98 (dd, J=12.7, 5.0 Hz, 1H), 2.77 (d, J=12.7 Hz, 1H), 2.63-2.50 (m, 4H), 2.34 (t, J=7.4 Hz, 2H), 2.24 (dd, J=16.8, 7.6 Hz, 6H), 1.86-1.38 (m, 34H); $^{19}$F-NMR (282 MHz, CD$_3$OD): δ −76.88, −76.93; HRMS (m/z): [M−2H]$^+$ calcd for C$_{59}$H$_{100}$F$_3$N$_{12}$O$_{15}$S, 1244.65; found 1242; IR (neat): 3293, 3084, 1626, 1547, 1461, 1364, 1256, 1116 cm$^{-1}$.

(g) Synthesis of 2,5-Dioxopyrrolidin-1-yl6-(3-{[(1S)-1-[(3-{2-[2-({9-[(3aS,4S,6aR)-2-oxo-hexahydro-1H-thieno[3,4-d]imidazolidin-4-yl]-5-oxononyl}oxy)ethoxy]ethoxy}propyl)carbamoyl]-5-[6-(6-{[6-(2,2,2-trifluoroacetohydrazido)pyridin-3-yl]formamido}hexanamido)hexanamido]pentyl]carbamoyl}propanamido)hexanoate (16)

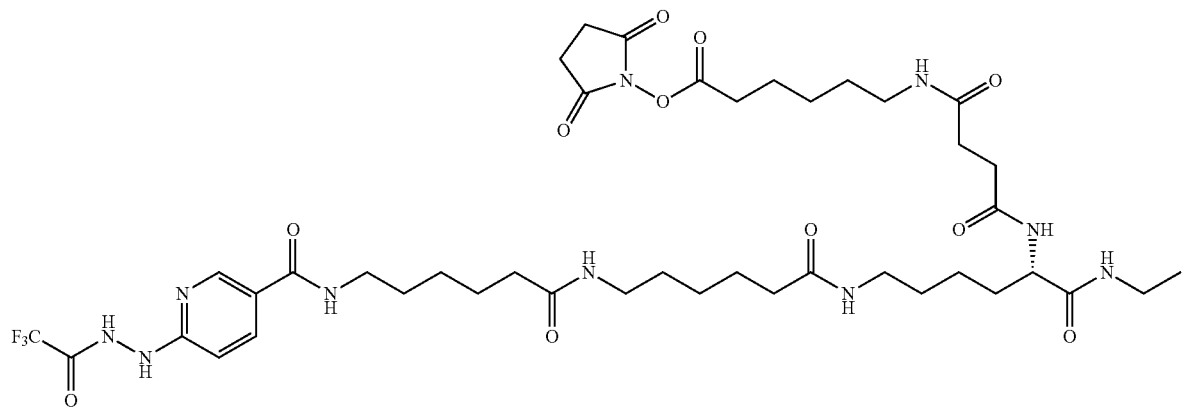

16

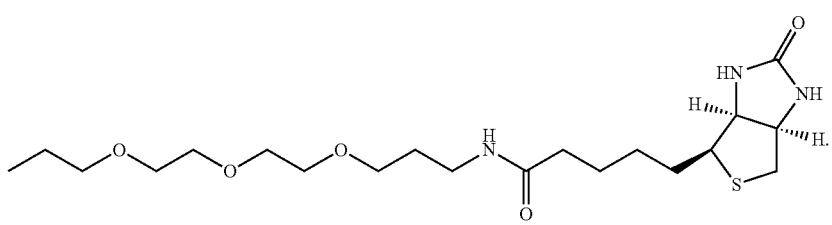

Compound 15 (28 mg, 23 µmol), NHS (3.1 mg, 27 µmol) and EDCI (5.6 mg, 27 µmol) were dissolved in DMF (0.3 mL) and then the reaction mixture was stirred overnight and the crude mixture was concentrated under reduced pressure and purified by sephadex LH-20 (CHCl$_3$/MeOH=95:5) providing the desired compound as a slightly green color viscous foam (19 mg, 62%).

TLC (CH$_2$Cl$_2$:MeOH:H$_2$O, 65:25:4 v/v): R$_F$=0.8; $^1$H-NMR (600 MHz, DMF-d$_7$): δ 9.46 (brs, 1H), 8.70 (d, J=2.2 Hz 1H), 8.33-8.25 (m, 1H), 8.14 (dd, J=8.8, 2.4 Hz, 1H), 8.01-7.99 (m, 2H), 7.95-7.93 (m, 1H), 7.91-7.85 (m, 1H), 7.78-7.71 (m, 3H), 7.15 (d, J=8.8 Hz, 1H), 6.41 (brs, 1H), 6.32 (brs, 1H), 4.47 (dd, J=6.9, 5.8 Hz, 1H), 4.31-4.29 (m, 1H), 4.27-4.23 (m, 1H), 3.59-3.45 (m, 12H), 3.336-3.32 (m, 2H), 3.24-3.12 (m, 11H), 2.93 (s, 4H), 2.73-2.69 (m, 2H), 2.54-2.42 (m, 4H), 2.18-2.13 (m, 8H), 1.86-1.29 (m, 34H); $^{19}$F-NMR (282 MHz, CD$_3$OD): δ −70.52, −75.60; HRMS (m/z): [M+Na+2H]$^+$ calcd for C$_{60}$H$_{94}$F$_3$N$_{13}$O$_{16}$S, 1341.66; found 1366; LCMS found 1343.3 [M+2H]$^+$; IR (neat): 3390, 3283, 2932, 2865, 1633, 1551, 1459, 1365, 1073 cm$^{-1}$.

Example 3

Ligand-Based Receptor Capturing with Insulin (a) Ligand Coupling to Trifunctional Cross-Linker Joy-05-125 (Obtained from Example 2)

50 µg Joy-05-125 (100 mM in DMSO) was added to 100 µg of insulin (I9278, Sigma-Aldrich) in 10 µl HEPES pH8.2 to obtain a ratio of cross-linker:ligand of approximately 2:1. For the control sample, 50 µg Joy-05-125 (100 mM in DMSO) was added to a quenching solution (10 mM Glycine in 10 µl HEPES pH8.2). Reactions were carried out for approximately 1 h at room temperature.

(b) Harvesting of Cells and Oxidation of Cell Surface Glycoproteins.

2×10$^8$ cells (Jurkat T) were collected in a 50 ml tube and washed with phosphate buffered saline (PBS, pH7.4). Subsequently, cells were oxidized for 15 min in the dark at 4° C. with 1.5 mM sodium-meta-periodate (Thermo Scientific) in labeling buffer (PBS, pH6.5). The cell pellet was washed once with 50 ml labeling buffer to remove most of the sodium-meta-periodate and to deplete dead cells/fragments.

(c) Ligand-Based Receptor Capturing

The cell pellet was resuspended in labeling buffer in two separate tubes (all the following steps were carried out in parallel for the ligand and the control reaction, respectively). Insulin coupled to Joy-05-125 and the quenched reagent were each added to 10$^8$ cells in 10 ml labeling buffer and incubated for 60 min at 4° C. on a slow rotator. Upon capturing, the cell pellet was washed with 50 ml PBS.

(d) Cell Lysis and Tryptic Digest

The cell pellets were resuspended in 1 ml 50 mM ammonium bicarbonate. Cells were lysed by indirect sonication (100% amplitude/0.8 cycle) in a VialTweeter (Hielscher) and the lysate was centrifuged at 2,500 g at 4° C. for 10 min to pellet cell nuclei. Supernatants were transferred to new tubes and the acid-labile surfactant RapiGest (Waters) was added to a final concentration of 0.1% followed by 5 min of indirect sonication to obtain a translucent solution. Samples were reduced with 5 mM TCEP (Thermo Scientific) for 30 min at room temperature followed by alkylation with 10 mM iodoacetamide (Thermo Scientific). 200 µg Trypsin (from bovine pancreas, Sigma Aldrich) was added and samples were digested over night on a slow rotator. Upon digestion, the peptide mixture was heated to 96° C. for 10 min to inactivate the proteases and undigested particles were removed by centrifugation for 10 min at 13000 g.

(e) Glycopeptide Capture and Release

2×50 µl of UltraLink Streptavidin Plus beads (Thermo Scientific) were washed twice with 50 mM ammonium bicarbonate in Mobicols (Bocascientific). The washed streptavidin beads were added to the peptide solutions and incubated for 1 h on a slow rotator. The captured glycopeptides were washed intensively with 10 ml 5 M sodium chloride, followed by 10 ml 1% Triton X-100 (Sigma) in 50 mM ammonium bicarbonate, followed by 10 ml 50 mM ammonium bicarbonate, followed by 10 ml 100 mM sodium carbonate pH 11, followed by 10 ml 100 mM ammonium bicarbonate which had been heated to 60° C. Washing was performed in Mobicols connected to a Vac-ManLaboratory Vacuum Manifold (Promega). Washed beads were incubated in 400 µl ammonium bicarbonate containing 2 µl PNGaseF (NEB) overnight in a slow rotator at 37° C. Upon incubation, the beads were washed once with 500 µl 50 mM ammonium bicarbonate and eluates were combined and dried in a speedvac for subsequent LC-MS/MS analysis.

(f) LC-MS Data Acquisition

Peptides were resolubilized in 2% acetonitrile, 0.1% formic acid and analyzed on an LTQ-Orbitrap XL mass spectrometer (Thermo Scientific) equipped with a nanoelectrospray ion source coupled to a Nano LC Ultra 1D Plus (Eksigent) system for chromatographic separation. Peptides were loaded on a capillary reversed-phase C18 column (75 µm inner diameter and 10 cm of bed length; 200 A, 3 µm C18 beads, Michrom BioResources). Reversed-phase chromatography was performed with a flow rate of 300 nl/min and a linear gradient elution of 2-40% B in 40 min with (A) 0.1% formic acid, 2% acetonitrile and (B) 0.1% formic acid, 98% acetonitrile. The MS instrument was operated in the data-dependent mode whereby 5 collision-induced dissociation (CID) MS/MS spectra were acquired in the linear ion trap per each FT-MS scan, the latter acquired at 60,000 FWHM resolution settings. Charge state screening was employed, including all multiple charged ions for triggering MS/MS attempts and excluding all singly charged precursor ions as well as ions for which no charge state could be determined. Only peptide ions exceeding a threshold of 250 ion counts were allowed to trigger MS/MS-scans, followed by dynamic exclusion for 5 seconds.

(g) Database Searching and Peptide/Protein Quantification

All MS/MS spectra were searched against the UniProtKB/Swiss-Prot database (Version 57.15) using the SEQUEST algorithm. Statistical analysis of the data was performed using a combination of ISB open source software tools (PeptideProphet, Protein Prophet (http://tools.proteomecenter.org/software.php)) and a PeptideProphet probability score of at least 0.8 was used to filter the data. For peptides containing the consensus N115-X-S/T glycosylation motif, label-free quantitative data analysis was performed using the Progenesis LC-MS software (Nonlinear Dynamics). Automatic retention time alignment was manually verified and feature outlines of formerly glycosylated peptides were corrected if necessary to guarantee accurate relative quantification between samples. Raw abundances for formerly glycosylated peptides were extracted and normalized to obtain an equal amount of total glycopeptide feature intensities in the ligand and control sample, respectively.

Figure 2:
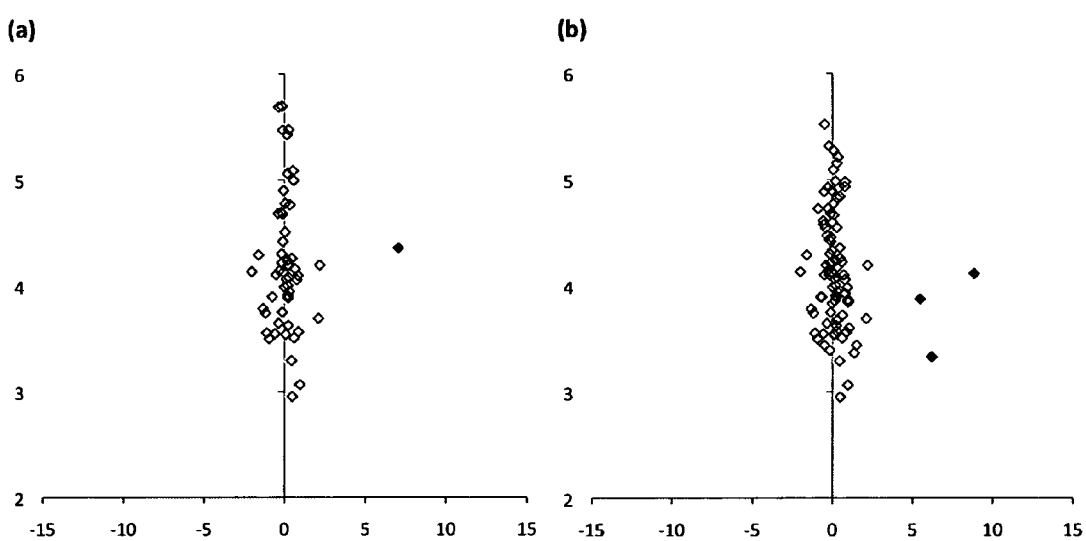
FIG. 2: Relative-quantitative evaluation of ligand-based receptor capturing with insulin.

Relative-quantitative evaluation of the data (see FIGS. 2(a) and (b)) revealed that the insulin receptor is the only protein identified as a specific receptor for insulin on Jurkat cells on the protein level (a) and peptide level (b), respectively. In FIGS. 2(a) and (b) the protein or peptide abundance is displayed along the y-axis as the log 10 of the higher abundance (insulin sample or control sample). In the x dimension, the log 2 of the ratio of insulin sample to control sample abundance reveals specific enrichments (insulin receptor protein/peptides are shown with filled black data points, other proteins/peptides with empty data points). Thereby, the peptide abundance is the sum of the peak areas within the isotope boundaries of a given glycopeptide feature. The protein abundance is the sum of the abundances of all glycopeptide ions which have been identified as coming from the same protein. Notably, the insulin receptor was identified with three different peptides, which adds a lot of confidence to the averaged high protein enrichment ratio.

Example 4

Ligand-Based Receptor Capturing with a CD44 Antibody (a) Ligand Coupling to Trifunctional Crosslinker Joy-05-125 (Obtained According to Example 2)

50 μg Joy-05-125 (100 mM in DMSO) was added to 100 μg of a monoclonal CD44 antibody (mouse IgG1, clone DB105, Miltenyi Biotec) in 50 μl HEPES pH8.2 to obtain a ratio of cross-linker:ligand of approximately 50:1. For the control sample, 50 μg Joy-05-125 (100 mM in DMSO) was added to a quenching solution (10 mM Glycine in 50 μl HEPES pH8.2). Reactions were carried out for approximately 1 h at room temperature.

(b) Harvesting of Cells and Oxidation of Cell Surface Glycoproteins

U-2 OS cells were cultivated on 6 Petri Dishes (140×20 mm) to reach about 50% confluency and washed with PBS. Subsequently, cells were oxidized for 15 min in the dark at 4° C. with 1.5 mM sodium-meta-periodate (Thermo Scientific) in labeling buffer (PBS, pH 6.5). Cells were washed with 20 ml labeling buffer per plate to remove most of the sodium-meta-periodate and to deplete dead cells/fragments.

(c) Ligand-Based Receptor Capturing

The cell pellet was resuspended in labeling buffer in two separate tubes (all the following steps were carried out in parallel for the ligand and the control reaction, respectively). The CD44 antibody coupled to Joy-05-125 and the quenched reagent were each added to 3 dishes in 5 ml labeling buffer per dish and incubated for 60 min at 4° C. on a slow shaker. Upon capturing, cells were washed with 20 ml PBS per plate.

(d) Cell Lysis and Tryptic Digest

The cells were detached from the Petri Dishes with 10 mM EDTA in PBS and washed once with PBS. Cell pellets were resuspended in 1 ml 50 mM ammonium bicarbonate. Cells were lysed by indirect sonication (100% amplitude/0.8 cycle) in a VialTweeter (Hielscher) and the lysate was centrifuged at 2,500 g at 4° C. for 10 min to pellet cell nuclei. Supernatants were transferred to new tubes and the acid-labile surfactant RapiGest (Waters) was added to a final concentration of 0.1% followed by 5 min of sonication to obtain a translucent solution. Samples were reduced with 5 mM TCEP (Thermo Scientific) for 30 min at room temperature followed by alkylation with 10 mM iodoacetamide (Thermo Scientific). 200 μs Trypsin (from bovine pancreas, Sigma Aldrich) was added and samples were digested overnight on a slow rotator. Upon digestion, the peptide mixture was heated to 96° C. for 10 min to inactivate the proteases and undigested particles were removed by centrifugation for 10 min at 13000 g.

The remaining steps of the protocol were carried out as described for Example 3.

Again, relative-quantitative evaluation of the data (see FIG. 3) revealed that the CD44 cell surface glycoprotein was the only protein identified as a specific target for the CD44 antibody on U-2 OS cells.

Figure 3:
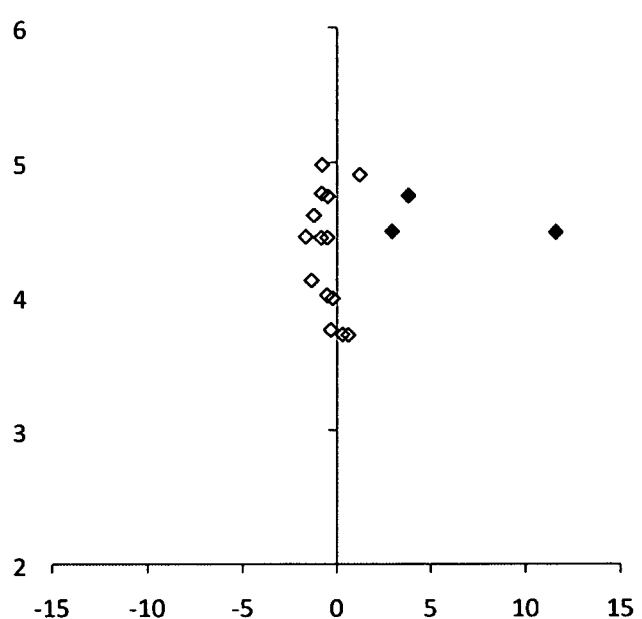
FIG. 3: Relative-quantitative evaluation of ligand-based receptor capturing with a CD44 antibody.

The results are illustrated in FIG. 3, wherein the peptide abundance is displayed along the y-axis as the log 10 of the higher abundance (CD44 antibody sample or control sample). In the x dimension, the log 2 of the ratio of antibody sample to control sample abundance reveals specific enrichments (CD44 peptides are shown with filled black data points, peptides derived from other proteins with empty data points). Thereby, the peptide abundance is the sum of the peak areas within the isotope boundaries of a given glycopeptide feature. Notably, CD44 was identified with three different peptides, which adds a lot of confidence to the averaged high protein enrichment ratio.

The invention claimed is:

1. A trifunctional crosslinking reagent of formula

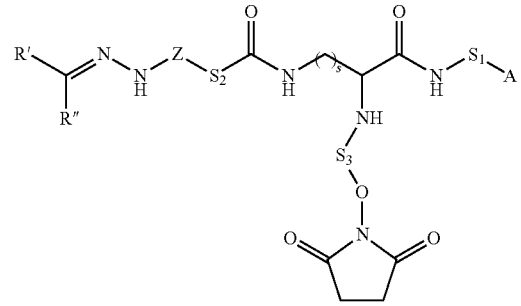

wherein s is from 1 to 12;

A is an affinity group selected from the group consisting of biotin and derivatives thereof, carbohydrates and glycans;

$S_1$, $S_2$, $S_3$ are independently of each other a liner chain comprising one or more repeating units of formula (a) and/or (b), or combinations thereof,

$Y_1$, $Y_2$, $Y_3$ are independently of each other a group selected from —O—, —CO—, COO—, —OCO—, —O—CO—O—, —OCH$_2$, CH$_2$O—, NR$_1$—, —NR$_1$—CO—, —CO—NR$_1$—;

$R_1$ represents H or (C1-C6)alkyl; and n, m, p, and q are independently of each other an integer from 1 to 10;

Z is aryl or heteroaryl, and

R', R" being selected from hydrogen, substituted (C1-C6) alkyl, substituted aryl and substituted heteroaryl, wherein R' and R" do not simultaneously represent hydrogen.

2. The trifunctional crosslinking reagent according to claim 1, wherein A is biotin.

3. The trifunctional crosslinking reagent according to claim 1, wherein Z is an aryl group selected from unsubstituted or substituted phenyl, naphthyl, and anthracenyl or a heteroaryl group selected from unsubstituted or substituted pyridyl, furyl, imidazolyl, benzimidazolyl, pyrimidinyl, thienyl, quinolinyl, indolyl, and thiazolyl.

4. A method of using a trifunctional crosslinking reagent according to claim 1 for characterizing and analyzing interactions between a ligand and a target glycoprotein receptor.

5. The method according to claim 4, wherein the target glycoprotein receptor is a cell surface or secreted glycoprotein.

6. A method of identifying specific interactions between a ligand and a target glycoprotein receptor having at least one carbohydrate residue in a sample, wherein the ligand recognizes a ligand-specific domain on the target glycoprotein receptor, comprising the steps of:
   i) providing a sample comprising said target glycoprotein receptor,
   ii) subjecting the target glycoprotein receptor to oxidative treatment to generate aldehyde functions on the at least one carbohydrate residue thereby obtaining an oxidized target glycoprotein receptor,
   iii) providing a trifunctional crosslinking reagent according to claim 1, and allowing the N-hydroxysuccinimide ester to conjugate to said ligand to obtain a ligand-crosslinking reagent-complex,
   iv) contacting the sample with the ligand-crosslinking reagent-complex under conditions under which (a) the ligand is able to bind to the ligand-specific domain on the target glycoprotein receptor and (b) the protected hydrazine group is converted to its free form and allowed to react with the oxidized target glycoprotein receptor, to obtain a dual peptide-bound complex,
   v) isolating and purifying the dual peptide-bound complex from the sample,
   vi) releasing the peptides from the purified dual peptide-bound complex obtained in step (iv) to obtain released peptides and
   vii) analyzing and quantifying the released peptides obtained in step (v) by high mass accuracy mass spectrometry, and
   viii) identifying the interactions between the ligand and the target glycoprotein receptor through quantitative comparison to a control reaction.

7. The method according to claim 6, wherein the glycoprotein is either in solution or on the surface of a cell.

8. The method according to claim 6, wherein A is biotin.

9. The method according to claim 6, wherein step (v) includes isolating and purifying the dual peptide-bound complex from the sample by first subjecting the sample to enzymatic digestion to obtain a processed cell sample followed by affinity purification of the processed cell sample.

10. The method according to claim 6, wherein step (vi) includes releasing the peptides from the purified dual peptide-bound complex obtained in step (v) by subjecting it to glycosidase treatment.

11. A kit comprising a trifunctional crosslinking reagent according to claim 1.

12. The method according to claim 4, wherein the ligand is selected from the group consisting of proteins, peptides, hormones, chemical molecules, pharmaceutical drugs and toxins.

13. The method according to claim 6, wherein the ligand is selected from the group consisting of proteins, peptides, hormones, chemical molecules, pharmaceutical drugs and toxins.

14. The method according to claim 10, wherein step (vi) includes releasing the peptides from the purified dual peptide-bound complex obtained in step (v) by subjecting it to treatment with a endoglycosidase to obtain released peptides.

* * * * *